United States Patent
Bi et al.

(10) Patent No.: US 9,951,015 B2
(45) Date of Patent: Apr. 24, 2018

(54) HETEROCYCLIC COMPOUNDS AND THEIR USES

(71) Applicants: AMGEN INC., Thousand Oaks, CA (US); CYTOKINETICS, INC., South San Francisco, CA (US)

(72) Inventors: Mingda Bi, Simi Valley, CA (US); Robert Kuehl, San Francisco, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/210,713

(22) Filed: Mar. 14, 2014

(65) Prior Publication Data
US 2014/0309235 A1    Oct. 16, 2014

Related U.S. Application Data

(60) Provisional application No. 61/785,763, filed on Mar. 14, 2013.

(51) Int. Cl.
| | |
|---|---|
| *C07D 213/75* | (2006.01) |
| *A61K 9/20* | (2006.01) |
| *A61K 31/496* | (2006.01) |
| *A61K 47/38* | (2006.01) |

(52) U.S. Cl.
CPC .......... *C07D 213/75* (2013.01); *A61K 9/2013* (2013.01); *A61K 9/2018* (2013.01); *A61K 9/2054* (2013.01); *A61K 31/496* (2013.01); *A61K 47/38* (2013.01)

(58) Field of Classification Search
CPC .. A61K 31/496; A61K 19/2054; A61K 47/38; A61K 9/2013; A61K 9/2018; C07D 213/75
See application file for complete search history.

(56) References Cited

U.S. PATENT DOCUMENTS

| | | | |
|---|---|---|---|
| 7,507,735 B2 * | 3/2009 | Morgan | C07D 211/56 514/252.13 |
| 2007/0161617 A1 * | 7/2007 | Morgan | A61K 31/496 514/210.2 |

OTHER PUBLICATIONS

Siepe et al. ("Strategies for the design of hydrophilic matrix tablets with controlled microenvironmental pH" in International Journal of Pharmaceutics 316 (2006) 14-20).*

* cited by examiner

*Primary Examiner* — Blessing M Fubara
(74) *Attorney, Agent, or Firm* — Marshall, Gerstein & Borun LLP

(57) ABSTRACT

Provided are certain pharmaceutical formulations of omecamtiv mecarbil and methods for their preparation and use.

33 Claims, 10 Drawing Sheets

|  | IR | MTX-F1 | MTX-F2 |
|---|---|---|---|
| Potency | 0.979 | 0.999 | 0.995 |
| $T_{max}$ (h)[#] | 0.5 (0.5 - 1) | 3 (1 -12) | 2.0 (1 -10) |
| $C_{max}$ (ng/mL) | 269 (30.7)<br>(138 – 449) | 56.2 (27.6)<br>(36.6 – 90.6) | 71.8 (28.9)<br>(48.3 – 139) |
| $AUC_{last}$ (ng.h/mL) | 2451 (20.0)<br>(1787 – 3565) | 1972 (20.0)<br>(1215 – 2930) | 2130 (30.0)<br>(1102 – 3849) |
| $AUC_{inf}$ (ng.h/mL) | 2509 (17.1)<br>(1819 – 3782) | 2142 (22.9)<br>(1248 – 3120) | 2178 (30.6)<br>(1176 – 4093) |
| $t_{1/2}$ (h) | 19 (20.6)<br>(12.2 – 25.3) | 21.7 (15.0)<br>(13.7 – 26.5) | 18.5 (24.9)<br>(8.66 – 29.1) |
| RBA<br>(rel to IR)* | -- | 0.76<br>[0.71 – 0.81] | 0.87<br>[0.81 – 0.93] | data presented as median (%CV) (range)

: median(range)

RBA: relative bioavailability; * Geo mean (90% CI)

HETEROCYCLIC COMPOUNDS AND THEIR USES

CROSS-REFERENCE TO RELATED APPLICATIONS

The benefit of U.S. Provisional Application No. 61/785,763, filed Mar. 14, 2014 is claimed, the disclosure of which is incorporated by reference in its entirety.

FIELD

Provided is a pharmaceutical formulation comprising omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydochloride hydrate.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

U.S. Pat. No. 7,507,735, herein incorporated by reference, discloses a genus of compounds, including omecamtiv mecarbil (AMG 423, CK-1827452), having the structure:

Omecamtiv mecarbil is a first in class direct activator of cardiac myosin, the motor protein that causes cardiac contraction. It is being evaluated as a potential treatment of heart failure in both intravenous and oral formulations with the goal of establishing a new continuum of care for patients in both the in-hospital and outpatient settings.

Clinical trials providing an I.V. delivery of omecamtiv mecarbil have shown that plasma levels of the drug can be delivered safely and effectively. However, standard release formulations and some extended release formulations gave peak to trough ratios that may be too great to provide a safe and effective amount of omecamtiv mecarbil to patients who need the drug in a chronic or preventative setting (See, FIG. 4). Accordingly, an effective sustained release formulation would be desirable for increased patient safety and effectiveness.

SUMMARY

Provided is a pharmaceutical formulation comprising:
omecamtiv mecarbil, or a pharmaceutically acceptable salt, a pharmaceutically acceptable hydrate, or a pharmaceutically acceptable hydrate of a pharmaceutically acceptable salt thereof;
a control release agent;
a pH modifying agent; a filler; and
a lubricant.

Also provided is a process for making a pharmaceutical formulation comprising:
blending a mixture comprising omecamtiv mecarbil, or a pharmaceutically acceptable salt, a pharmaceutically acceptable hydrate, or a pharmaceutically acceptable hydrate of a pharmaceutically acceptable salt thereof, a control release agent, a pH modifying agent, and a filler;
lubricating the blended mixture using a lubricant;
granulating the lubricated blend;
lubricating the resultant granulation using the lubricant; and
compressing the lubricated granulation into desired form.

Also provided is a method of treating a disease selected from acute heart failure and chronic heart failure, comprising administering a pharmaceutical formulation described herein to a patient in need thereof.

DESCRIPTION OF THE FIGURES

FIG. 5 is a table with data for an immediate release composition (IR) and two matrix modified release compositions (MTX-F1 and MTX-F2).

DETAILED DESCRIPTION

Figure 1:
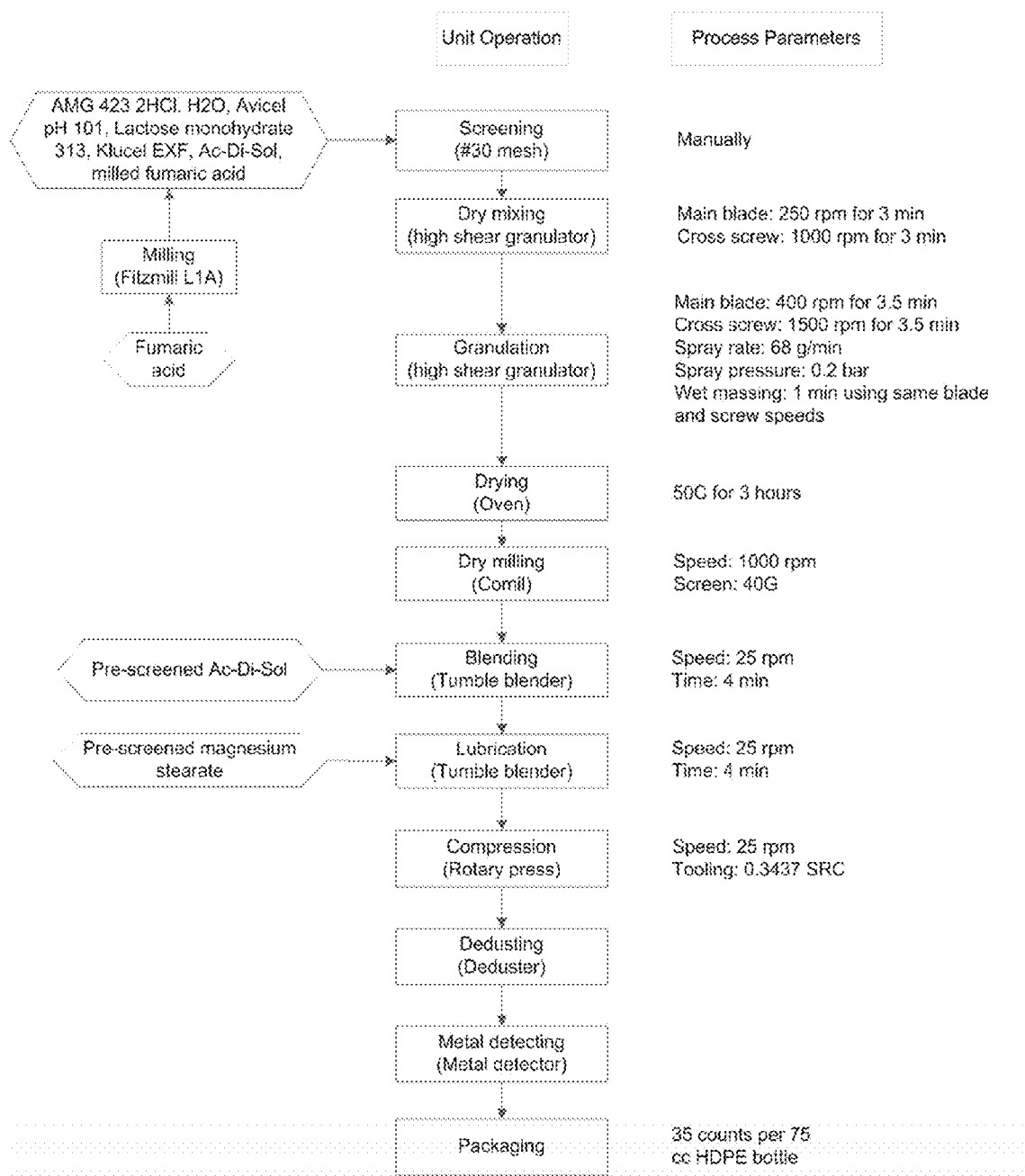
FIG. 1 is a flow diagram for the preparation of immediate release (IR) tablets of omecamtiv mecarbil (25 mg); see Example 1.

Unless otherwise specified, the following definitions apply to terms found in the specification and claims:

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of preventative treatment, such as, for example, chronic heart failure.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

"Pharmaceutically acceptable salts" include, but are not limited to salts with inorganic acids, such as hydrochlorate (i.e., hydrochloride), phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable addition salts.

The term "hydrate" refers to the chemical entity formed by the interaction of water and a compound, including, for example, hemi-hydrates, monohydrates, dihydrates, trihydrates, etc.

"Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Provided is a pharmaceutical formulation comprising omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydochloride hydrate.

The pharmaceutical formulations described herein are capable of releasing omecamtiv mecarbil evenly at a pace controlled by the diffusion of omecamtiv mecarbil through a gel layer formed by the hydration of the control release agents in the tablets. In some embodiments, in conjunction with other above or below embodiments, the present modified release matrix tablets demonstrate a minimal pH-dependent release in-vitro. In some embodiments, in conjunction with other above or below embodiments, complete release of omecamtiv mecarbil is achieved in both pH 2 and 6.8 dissolution medium within 24 hours, possibly resulting in less inter- and intra-subject variability and food effect. It is found that the present modified release matrix tablet dosage form is superior to the former immediate release dosage form in minimizing the plasma peak-trough ratio. As a result, the present modified release matrix tablets reduce plasma concentration fluctuation, leading to reduced side effects, and improved safety and efficacy. It is also expected that the present modified release matrix tablets will improve patient compliance by reducing the dosing frequency. Additionally, the present modified release matrix tablets are physicochemically stable—resulting in no physical attribute, assay, impurity, or dissolution profile changes after storage at 40° C./75% RH for 6 months.

In some embodiments, in conjunction with other above or below embodiments, the exposure of omecamtiv mecarbil from two to twelve hours after dosing in humans is between 40 and 70 ng/ml.

In some embodiments, in conjunction with other above or below embodiments, the exposure of omecamtiv mecarbil- from two to twelve hours after dosing in humans remains between 40 and 55 ng/ml.

In some embodiments, in conjunction with other above or below embodiments, the omecamtiv mecarbil is released in the following intervals:
  ≤30% dose dissolved at 1 hour;
  30-75% dose dissolved at 3 hours; and
  ≥80% dose dissolved at 12 hours.

In some embodiments, in conjunction with other above or below embodiments, the omecamtiv mecarbil is released in the following intervals:
  ≤30% dose dissolved at 2 hours;
  30-75% dose dissolved at 6 hours; and
  ≥80% dose dissolved at 16 hours.

Provided is a pharmaceutical formulation comprising:
  omecamtiv mecarbil, or a pharmaceutically acceptable salt, a pharmaceutically acceptable hydrate, or a pharmaceutically acceptable hydrate of a pharmaceutically acceptable salt thereof;
  a control release agent;
  a pH modifying agent;
  a filler; and
  a lubricant.

In some embodiments, in conjunction with other above or below embodiments, the pharmaceutical formulation comprises about
  3-30% w/w of omecamtiv mecarbil, or a pharmaceutically acceptable salt, a pharmaceutically acceptable hydrate, or a pharmaceutically acceptable hydrate of a pharmaceutically acceptable salt thereof;
  15-35% w/w control release agent;
  20-45% w/w pH modifying agent;
  25-65% w/w filler; and
  0.1-1.0% w/w lubricant.

In some embodiments, in conjunction with other above or below embodiments, the pharmaceutical formulation comprises about 12-25 (w/w %) omecamtiv mecarbil Di-HCl hydrate; 25-35 (w/w %) Methocel™ K100 M Prem CR; 20-30 (w/w %) microcrystalline cellulose, PH 102; 5-10 (w/w %) lactose monohydrate, FF 316; 12-25 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation comprises about:

3-10 (w/w %) omecamtiv mecarbil Di-HCl hydrate; 20-40 (w/w %) Methocel™ K100 M Prem CR; 30-42 (w/w %) microcrystalline cellulose, PH 102; 12-25 (w/w %) lactose monohydrate, FF 316; 4-11 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation comprises about:

12-25 (w/w %) omecamtiv mecarbil Di-HCl hydrate; 1-10 (w/w %) Methocel™ K100 M Prem CR; 12-27 (w/w %) Methocel™ K100 LV Prem CR; 20-35 (w/w %) microcrystalline cellulose, PH 102; 4-15 (w/w %) lactose monohydrate, FF 316; 12-25 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation comprises about:

3-10 (w/w %) omecamtiv mecarbil Di-HCl hydrate; 1-10 (w/w %) Methocel™ K100 M Prem CR; 12-27 (w/w %) Methocel™ K100 LV Prem CR; 30-50 (w/w %) microcrystalline cellulose, PH 102; 15-25 (w/w %) lactose monohydrate, FF 316; 3-11 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation comprises about:

18-19 (w/w %) omecamtiv mecarbil Di-HCl hydrate; 28-32 (w/w %) Methocel™ K100 M Prem CR; 23-26 (w/w %) microcrystalline cellulose, PH 102; 7-9 (w/w %) lactose monohydrate, FF 316; 17-20 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation comprises about:

5-7 (w/w %) omecamtiv mecarbil Di-HCl hydrate; 27-33 (w/w %) Methocel™ K100 M Prem CR; 35-38 (w/w %) microcrystalline cellulose, PH 102; 17-20 (w/w %) lactose monohydrate, FF 316; 6-9 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation comprises about:

17-20 (w/w %) omecamtiv mecarbil Di-HCl hydrate; 3-7 (w/w %) Methocel™ K100 M Prem CR; 18-22 (w/w %) Methocel™ K100 LV Prem CR; 26-30 (w/w %) microcrystalline cellulose, PH 102; 8-11 (w/w %) lactose monohydrate, FF 316; 17-20 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation comprises about:

5-7 (w/w %) omecamtiv mecarbil Di-HCl hydrate; 3-7 (w/w %) Methocel™ K100 M Prem CR; 18-22 (w/w %) Methocel™ K100 LV Prem CR; 37-43 (w/w %) microcrystalline cellulose, PH 102; 18-22 (w/w %) lactose monohydrate, FF 316; 6-9 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation comprises about:

18.37 (w/w %) omecamtiv mecarbil Di-HCl hydrate; 30 (w/w %) Methocel™ K100 M Prem CR; 24.20 (w/w %) microcrystalline cellulose, PH 102; 8.07 (w/w %) lactose monohydrate, FF 316; 18.37 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation comprises about:

6.13 (w/w %) omecamtiv mecarbil Di-HCl hydrate; 30 (w/w %) Methocel™ K100 M Prem CR; 36.81 (w/w %) microcrystalline cellulose, PH 102; 18.40 (w/w %) lactose monohydrate, FF 316; 7.66 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation comprises about:

18.37 (w/w %) omecamtiv mecarbil Di-HCl hydrate; 5 (w/w %) Methocel™ K100 M Prem CR; 20 (w/w %) Methocel™ K100 LV Prem CR; 27.95 (w/w %) microcrystalline cellulose, PH 102; 9.31 (w/w %) lactose monohydrate, FF 316; 18.37 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation comprises about:

6.13 (w/w %) omecamtiv mecarbil Di-HCl hydrate; 5 (w/w %) Methocel™ K100 M Prem CR; 20 (w/w %) Methocel™ K100 LV Prem CR; 40.14 (w/w %) microcrystalline cellulose, PH 102; 20.07 (w/w %) lactose monohydrate, FF 316; 7.66 (w/w %) fumaric acid; 0.5 (w/w %) intra-granular magnesium stearate; and 0.5 (w/w %) extra-granular magnesium stearate.

Omecamtiv Mecarbil

In some embodiments, in conjunction with other above or below embodiments, the drug formulation comprises omecamtiv mecarbil dihydrochloride salt. In some embodiments, in conjunction with other above or below embodiments, the drug formulation comprises omecamtiv mecarbil dihydrochloride hydrate. In some embodiments, in conjunction with other above or below embodiments, the drug formulation comprises omecamtiv mecarbil dihydrochloride hydrate Form A.

Figure 7:
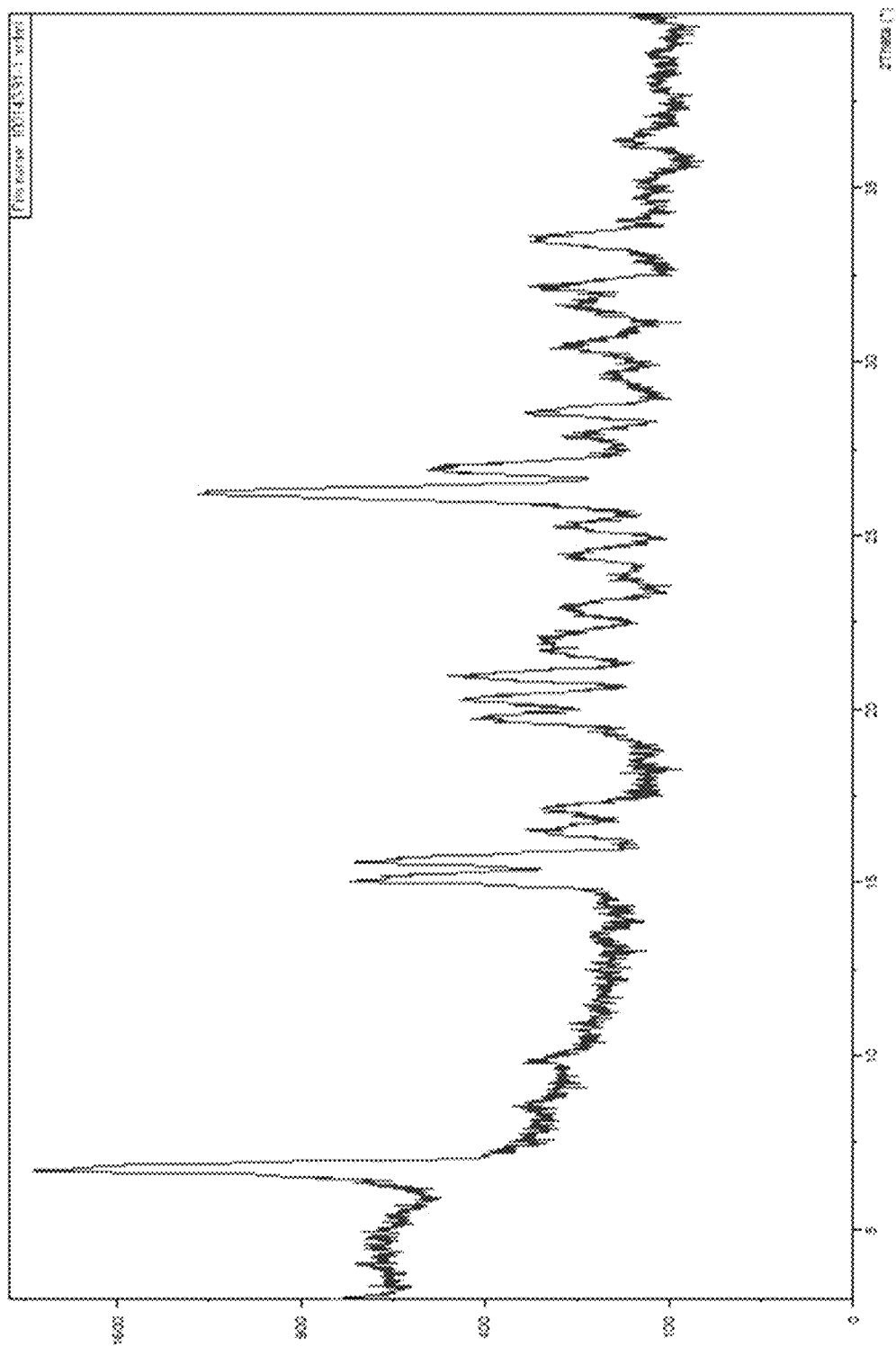
FIG. 7 shows an X-ray powder diffraction pattern (XRPD) for Form A.

In some embodiments, in conjunction with other above or below embodiments, Form A can be characterized by an X-ray powder diffraction pattern, obtained as set forth in the Examples, having peaks at about 6.6, 14.9, 20.1, 21.4, and 26.8±0.2° 2θ using Cu Kα radiation. Form A optionally can be further characterized by an X-ray powder diffraction pattern having additional peaks at about 8.4, 24.2, 26.0, 33.3±0.2° 2θ using Cu Kα radiation. Form A optionally can be even further characterized by an X-ray powder diffraction pattern having additional peaks at about 6.2, 9.7, 13.2, 14.3, 15.4, 16.3, 16.9, 18.9, 19.5, 20.7, 21.8, 22.8, 23.6, 25.1, 27.3, 27.7, 28.4, 29.4, 30.2, 31.2, 31.5, 31.9, 33.9, 34.5, 34.9, 36.1, 36.8, 37.7, 38.5, and 39.7±0.2° 2θ using Cu Kα radiation. In various cases, Form A can be characterized by an XRPD pattern having peaks at about 6.2, 6.6, 8.4, 9.7, 13.2, 14.3, 14.9, 15.4, 16.3, 16.9, 18.9, 19.5, 20.1, 20.7, 21.4, 21.8, 22.8, 23.6, 24.3, 25.1, 26.0, 26.8, 27.3, 27.7, 28.4, 29.4, 30.2, 31.2, 31.5, 31.9, 33.3, 33.9, 34.5, 34.9, 36.1, 36.8, 37.7, 38.5, and 39.7±0.2° 2θ using Cu Kα radiation. In some embodiments, in conjunction with other above or below embodiments, Form A can be characterized by an X-ray powder diffraction pattern substantially as depicted in FIG. 7. It is well known in the field of XRPD that while relative peak heights in spectra are dependent on a number of factors, such as sample preparation and instrument geometry, peak positions are relatively insensitive to experimental details.

Figure 8:
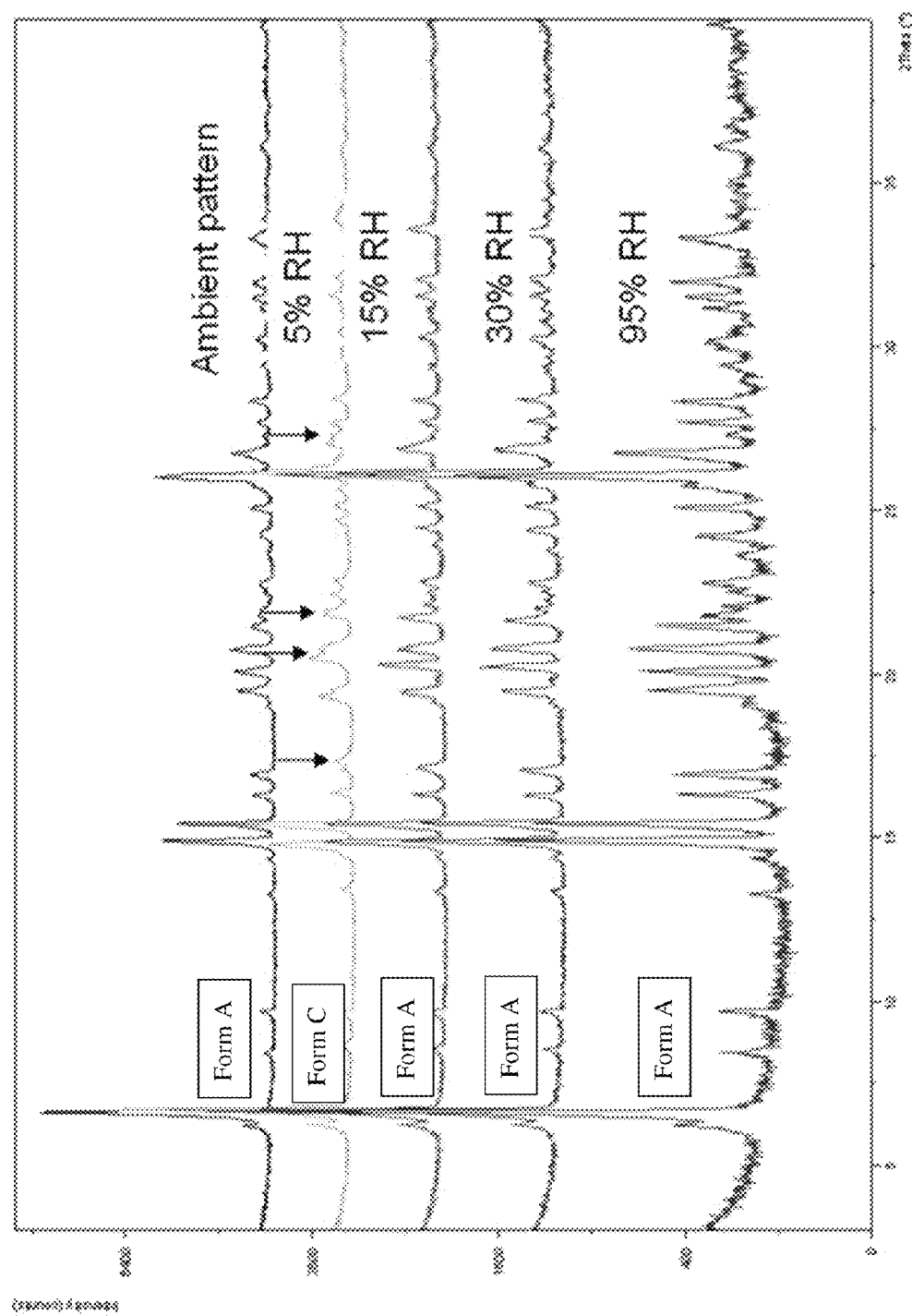
FIG. 8 shows an XRPD of a omecamtiv mecarbil dihydrochloride hydrate salt form at varying relative humidity conditions.
Figure 9:
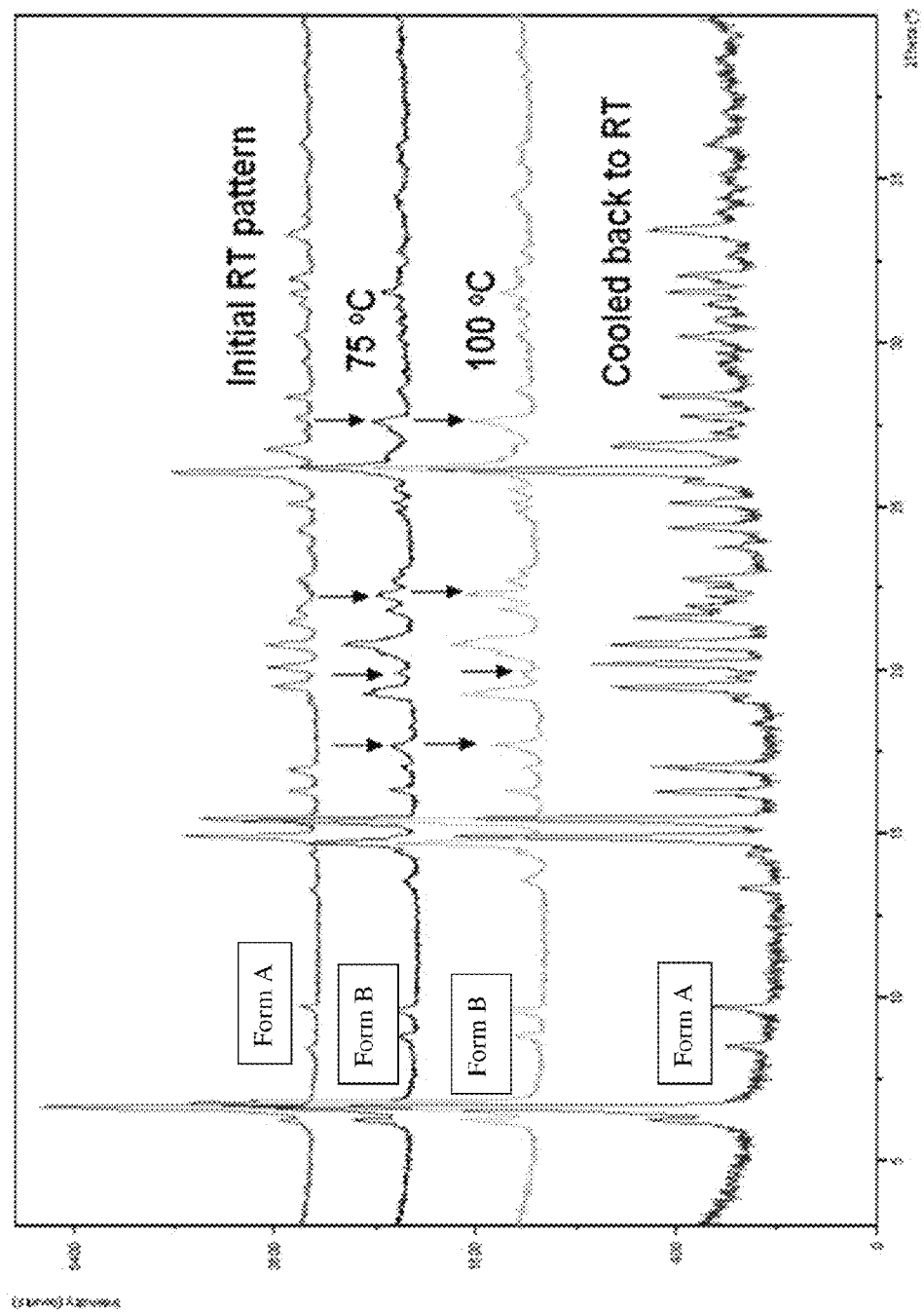
FIG. 9 shows an XRPD of a omecamtiv mecarbil dihydrochloride hydrate salt form at varying temperatures.

Form B and Form C polymorphs of omecamtiv mecarbil, are metastable anhydrous dihydrochloride forms, and can be formed under varied hydration conditions and temperatures, as noted in FIGS. 8 and 9. Characteristic Form B 2-theta values include 6.8, 8.8, 14.7, 17.7, and 22.3±0.2° 2θ using Cu Kα radiation, and can additionally include peaks at 9.6, 13.5, 19.2, 26.2±0.2° 2θ using Cu Kα radiation. Form B can be characterized with XRPD pattern peaks at 6.2, 6.8, 8.8, 9.6, 13.5, 14.4, 14.7, 15.4, 16.3, 17.0, 17.7, 18.3, 19.2, 19.9, 20.5, 20.8, 21.8, 22.3, 22.7, 23.0, 24.8, 25.1, 25.5, 26.2, 26.4, 26.8, 27.5, 28.5, 30.2, 30.6, 31.1, 31.5, 32.1, 32.7, 34.1, 34.4, 35.5, 35.9, 38.1, 38.9±0.2° 2θ using Cu Kα radiation. Characteristic Form C 2-theta values include 6.7, 14.8, 17.4, 20.6, and 26.2±0.2° 2θ using Cu Kα radiation, and can additionally include peaks at 8.7, 22.0, 27.1, and 27.7±0.2° 2θ using Cu Kα radiation. Form C can be characterized with XRPD pattern peaks at 6.2, 6.7, 8.7, 9.6, 13.5, 14.5, 14.8, 15.4, 16.4, 17.1, 17.4, 18.4, 19.3, 19.5, 19.9, 20.6, 20.8, 21.8, 22.0, 22.5, 22.8, 24.3, 24.7, 25.1, 25.6, 26.2, 26.5, 27.1, 27.3, 27.7, 28.5, 30.0, 30.5, 31.0, 31.5, 32.2, 32.8, 34.1, 35.2, 36.0, 36.9, and 38.8±0.2° 2θ using Cu Kα radiation.

Figure 10:
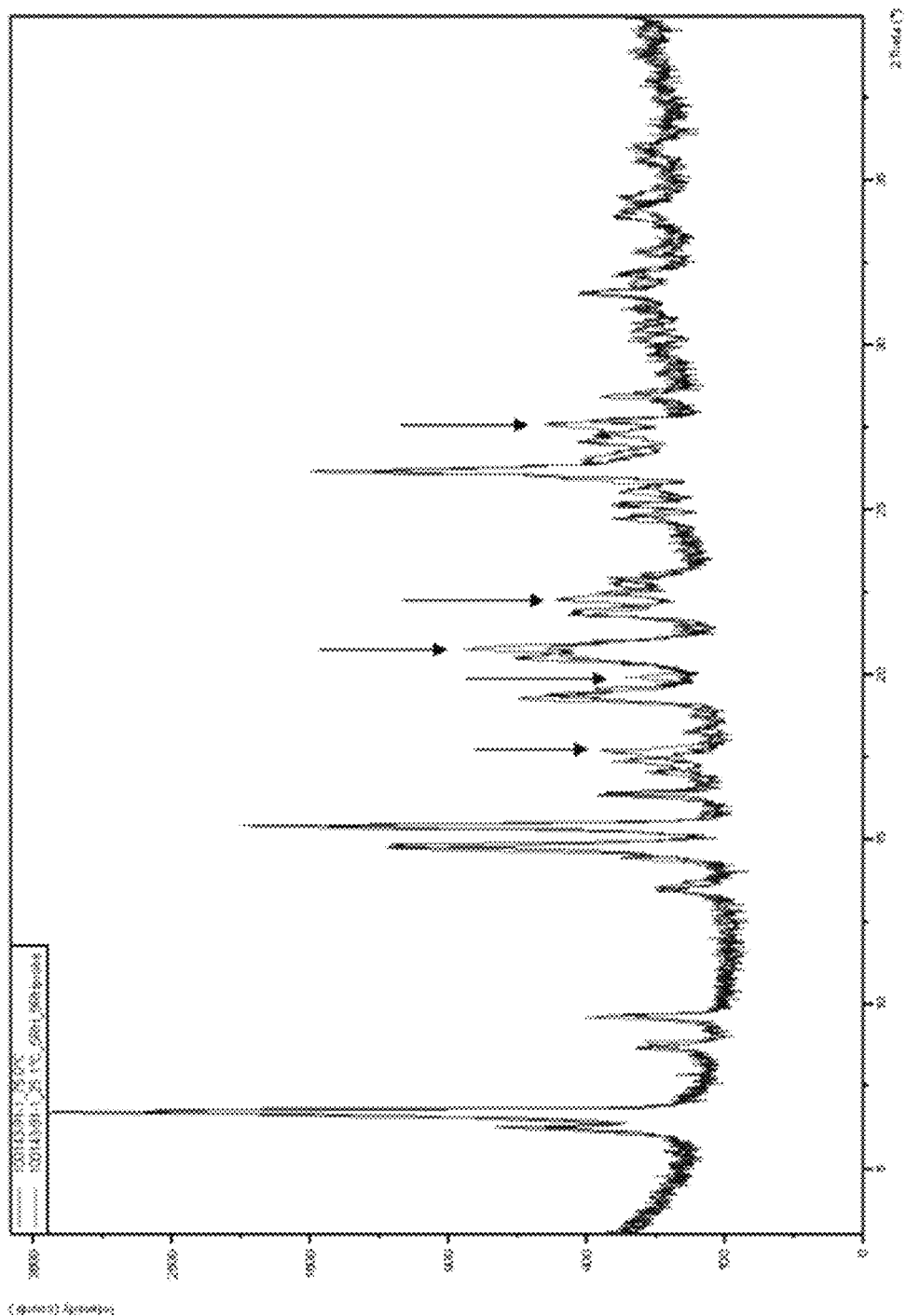
FIG. 10 shows an overlay of XRPD patterns for Forms A, B and C of omecamtiv mecarbil dihydrochloride salt.

See, also, FIG. 9 (variable temperature XRPD data), FIG. 8 (variable relative humidity XRPD data), and FIG. 10 (overlay)

Control Release Agent

As used herein, the term "control release agents" refer to agents that facilitate the release of the active ingredient from the present composition in a controlled fashion. In some embodiments, in conjunction with other above or below embodiments, the control release agents form a gel upon hydration. Control release agents include pulluan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethylmethacrylate, a copolymer of 2-methyl-5-vinylpyridine/methylmethacrylate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly(vinyl pyrolidone), starch and starch-based polymers, poly(2-ehtyl-2-oxazoline), poly(ethyleneimine), polyurethane hydrogels, welan gum, rhamsan gum, polyvinyl acetates, ethylcellulose, eudragit RL, RS, NE 30D, Kollicoat EMM 30D, or combinations thereof.

In some embodiments, in conjunction with other above or below embodiments, the control release agent is a polymer.

In some embodiments, in conjunction with other above or below embodiments, the control release agent is selected from pulluan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethyl methacrylate, a copolymer of 2-methy-5vinylpyrid¬ine/methylmethacrylate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly(vinyl pyrolidone), starch and starch-based polymers, poly(2-ehtyl-2-oxazoline), poly(ethyleneimine), polyurethane hydrogels, welan gum, rhamsan gum, polyvinyl acetates, ethylcellulose, eudragit RL, RS, NE 30D, and Kollicoat EMM 30D, or any combination thereof.

pH Modifying Agent

As used herein, the term "pH modifying agent" refers to an agent capable of modulating the pH to a desired range. In some embodiments, in conjunction with other above or below embodiments, the pH modifying agent is an acidifying agent. In some embodiments, in conjunction with other above or below embodiments, the pH modifying agent is present in an amount sufficient to lower the pH. pH Modulation agents include maleic acid, citric acid, tartaric acid, pamoic acid, fumaric acid, salicylic acid, 2,6-diaminohexanoic acid, camphorsulfonic acid, glycerophosphoric acid, 2-hydroxyethanesulfonic acid, isethionic acid, succinic acid, carbonic acid, p-toluenesulfonic acid, aspartic acid, 8-chloro-itheophylline, benezenesulfonic acid, malic acid, orotic acid, oxalic acid, benzoic acid, 2-naphthalenesulfonic acid, stearic acid, adipic acid, p-amino-isalicylic acid, 5-aminoslicylic acid, ascorbic acid, sulfuric acid, cyclamic acid, sodium lauryl sulfate, glucoheptonic acid, glucuronic acid, glycine, sulfuric acid, mandelic acid, 1,5-naphthalenedisulfonic acid, nicotinic acid, oleic acid, 2-oxoglutaric acid, pyridoxal 5-phosphate, undecanoic acid, p-acetamidobenzoic acid, o-acetamido-benzoic acid, m-acetamidobenzoic acid, N-acetyl-L-aspartic acid, camphoric acid, dehydrocholic acid, malonic acid, edetic acid, ethylenediainetetraacetic acid, ethylsulfuric acid, hydroxyphenylbenzoylbenzoic acid, glutamic acid, glycyrrhizic acid, 4-hexylresorcinol, hippuric acid, p-phenolsulfonic acid, 4-hydroxybenzoic acid, 3-hydroxybenzoic acid, 3-hydroxy-2-naphthoic acid, 1-hydroxy-2naphthoic acid, lactobionic acid, 3'-adenylic acid, 5'-adenylic acid, mucic acid, galactaric acid, pantothenic acid, pectic acid, polygalacturonic acid, 5-sulfosalicylic acid, 1,2,3,6-tetrahydro-1,3-dimethyl-2,6-dioxopurine-7-propanesulfonic acid, terephthalic acid, 1-hydroxy-2naphthoic acid, and combinations thereof. In some embodiments, in conjunction with other above or below embodiments, acidic excipients include, for example, maleic acid, citric acid, malic acid, fumaric acid, sulfuric acid, tartaric acid, lactoic acid, salicylic acid, aspartic acid, aminosalicylic acid, malonic acid, glutamic acid, and combinations thereof.

In some embodiments, in conjunction with other above or below embodiments, pH modifying agent includes maleic acid, citric acid, tartaric acid, pamoic acid, fumaric acid, salicylic acid, 2,6-diaminohexanoic acid, camphorsulfonic acid, glycerophosphoric acid, 2-hydroxyethanesulfonic acid, isethionic acid, succinic acid, carbonic acid, p-toluenesulfonic acid, aspartic acid, 8-chlorotheophylline, benezenesulfonic acid, malic acid, orotic acid, oxalic acid, benzoic acid, 2-naphthalenesulfonic acid, stearic acid, adipic acid, p-amino-salicylic acid, 5-aminoslicylic acid, ascorbic acid, sulfuric acid, cyclamic acid, sodium lauryl sulfate, glucoheptonic acid, glucuronic acid, glycine, sulfuric acid, mandelic acid, 1,5-naphthalenedisulfonic acid, nicotinic acid, oleic acid, 2-oxoglutaric acid, pyridoxal 5-phosphate, undecanoic acid, p-acetamidobenzoic acid, o-acetamidobenzoic acid, m-acetamidobenzoic acid, N-acetyl-L-aspartic acid, camphoric acid, dehydrocholic acid, malonic acid, edetic acid, ethylenediainetetraacetic acid, ethylsulfuric acid, hydroxyphenylbenzoylbenzoic acid, glutamic acid, glycyrrhizic acid, 4-hexylresorcinol, hippuric acid, p-phenolsulfonic acid, 4-hydroxybenzoic acid, 3-hydroxybenzoic acid, 3-hydroxy-2-naphthoic acid, 1-hydroxy-2naphthoic acid, lactobionic acid, 3'-adenylic acid, 5'-adenylic acid, mucic acid, galactaric acid, pantothenic acid, pectic acid, polygalacturonic acid, 5-sulfosalicylic acid, 1,2,3,6-tetrahydro-1, 3-dimethyl-2,6-dioxopurine-7-propanesulfonic acid, terephthalic acid, 1-hydroxy-2naphthoic acid, and combinations thereof.

In some embodiments, in conjunction with other above or below embodiments, the pH modifying agent is selected from maleic acid, citric acid, malic acid, fumaric acid, sulfuric acid, tartaric acid, lactoic acid, salicylic acid, aspartic acid, aminosalicylic acid, malonic acid, glutamic acid, and any combination thereof.

In some embodiments, in conjunction with other above or below embodiments, fumaric acid was used as the pH modifying agent as it is less hygroscopic and more compatible with omecamtiv mecarbil dihydrochloride hydrate than citric acid, resulting in less or no active form transformation and no changes in tablet appearance when stored at 40° C./75% RH for 6 months, leading to improved final product quality. Additionally, fumaric acid is more acidic (2-fold) than citric acid. Therefore, it is more efficient, i.e., 1:1 weight ratio to active instead of 2:1, to use fumaric acid to modulate the microenvironmental pH to enhance omecamtiv mecarbil release at neutral environment. Fumaric acid also has a very slow dissolution rate. As a result, fumaric acid will stay in the tablet longer and maintain the low microenvironmental pH better, resulting in more complete release of omecamtiv mecarbil within 24 hours.

Filler

As used herein, the term "fillers" refers to one or more substances that can be added to components of a pharmaceutical composition to increase bulk weight of the material to be formulated, e.g. tabletted, in order to achieve the desired weight. Fillers include but are not limited to starches, lactose, mannitol (such as Pearlitol™ SD 200), cellulose derivatives, calcium phosphate, sugar and the like.

Different grades of lactose include, but are not limited to, lactose monohydrate, lactose DT (direct tabletting), lactose anhydrous, Flowlac™ (available from Meggle products), Pharmatose™ (available from DMV) and others. Different grades of starches include, but are not limited to, maize starch, potato starch, rice starch, wheat starch, pregelatinized starch (commercially available as PCS PC 10 from Signet Chemical Corporation) and Starch 1500, Starch 1500 LM grade (low moisture content grade) from Colorcon, fully pregelatinized starch (commercially available as National 78-1551 from Essex Grain Products) and others. Different cellulose compounds that can be used include crystalline cellulose and powdered cellulose. Examples of crystalline cellulose products include but are not limited to CEOLUS™ KG801, Aviceff PH 101, PH102, PH301, PH302 and PH-F20, microcrystalline cellulose 114, and microcrystalline cellulose 112. Other useful fillers include, but are not limited to, carmellose, sugar alcohols such as mannitol, sorbitol and xylitol, calcium carbonate, magnesium carbonate, dibasic calcium phosphate, and tribasic calcium phosphate.

In some embodiments, in conjunction with other above or below embodiments, the filler is selected from starch, lactose, mannitol (such as Pearlitol™ SD 200), cellulose derivatives, calcium phosphate, and a sugar.

In some embodiments, in conjunction with other above or below embodiments, the filler is lactose anhydrous or lactose monohydrate. In some embodiments, in conjunction with other above or below embodiments, the filler is lactose DT, Flowlac™, or Pharmatose™.

In some embodiments, in conjunction with other above or below embodiments, the filler is maize starch, potato starch, rice starch, wheat starch, pregelatinized starch (such as Starch 1500 or Starch 1500 LM grade (low moisture content grade)), or fully pregelatinized starch.

In some embodiments, in conjunction with other above or below embodiments, the filler is microcrystalline cellulose, such as CEOLUS™ KG801, Avicel™ PH 101, PH102, PH301, PH302 and PH-F20, microcrystalline cellulose 114, or microcrystalline cellulose 112.

In some embodiments, in conjunction with other above or below embodiments, the filler is carmellose, mannitol, sorbitol, xylitol, calcium carbonate, magnesium carbonate, dibasic calcium phosphate, or tribasic calcium phosphate.

Lubricant

As used herein, the term "lubricants" refers to one or more substances that can be added to components of the present compositions to reduce sticking by a solid formulation to the equipment used for production of a unit doss form. Lubricants include stearic acid, hydrogenated vegetable oils, hydrogenated soybean oil and hydrogenated soybean oil & castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearylFumarate, DL-leucine, colloidal silica, and mixtures thereof.

In some embodiments, in conjunction with other above or below embodiments, the lubricant is stearic acid, hydrogenated vegetable oil, hydrogenated soybean oil, hydrogenated soybean oil, castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearylfumarate, DL-leucine, colloidal silica, or any mixture thereof.

Manufacturing Process

Also provided is a process for making a pharmaceutical formulation described herein, comprising:

blending a mixture comprising omecamtiv mecarbil, or a pharmaceutically acceptable salt, a pharmaceutically acceptable hydrate, or a pharmaceutically acceptable hydrate of a pharmaceutically acceptable salt thereof, a control release agent, a pH modifying agent, and a filler;

lubricating the blended mixture using a lubricant;

granulating the lubricated blend;

lubricating the resultant granulation using the lubricant; and compressing the lubricated granulation into desired form.

Also provided is a process for making a pharmaceutical formulation described herein, comprising:

providing a blended mixture comprising omecamtiv mecarbil, or a pharmaceutically acceptable salt, a pharmaceutically acceptable hydrate, or a pharmaceutically acceptable hydrate of a pharmaceutically acceptable salt thereof, a control release agent, a pH modifying agent, a filler, and a lubricant;

granulating the blended mixture; and compressing the lubricated granulation into desired form.

Also provided is a process for making a pharmaceutical formulation described herein, comprising:

compressing a granulation of omecamtiv mecarbil, or a pharmaceutically acceptable salt, a pharmaceutically acceptable hydrate, or a pharmaceutically acceptable hydrate of a pharmaceutically acceptable salt thereof, a control release agent, a pH modifying agent, a filler, and a lubricant into desired form.

In some embodiments, in conjunction with other above or below embodiments, the modified release matrix tablets are manufactured using dry granulation. The dry granulation process can help to avoid the active form transformation in the modified release matrix tablets. In addition, dry granulation process avoids issues observed in a high shear wet granulation process.

Also provided is a pharmaceutical formulation prepared by any of the processes described herein.

Stability

Forced degradation conditions (e.g., 40° C. and 75% relative humidity) are used to evaluate the long-term storage stability of a pharmaceutical ingredient or composition. In general terms, a stable composition is one which, after being subjected to forced degradation conditions, comprises the pharmaceutically active ingredients in an amount, for example 95%, relative to the amount initially present in the particular composition. Stability may be determined, using forced degradation or other methods, for periods of 1 week, 1 month, 2 months, 3 months, 4 months, 5 months, 6 months, 9 months, 12 months, 15 months, 18 months, 24 months, 30 months, 36 months, longer.

Assays for evaluating the stability of a pharmaceutical composition, such as those described herein, are known in the pharmaceutical arts. For example, one can determine the percentage of active pharmaceutical ingredients present in a given composition, as well as the presence and percentage of impurities, through the use of standard analytical techniques.

Methods of Treatment/Use of Formulations Disclosed

Also provided is a method for the use of such pharmaceutical formulations for the treatment of heart failure, including but not limited to: acute (or decompensated) congestive heart failure, and chronic congestive heart failure; particularly diseases associated with systolic heart dysfunction.

EXAMPLES

Manufacture of Omecamtiv Mecarbil Dihydrochloride Hydrate

Synthetic Route to Omecamtiv Mecarbil

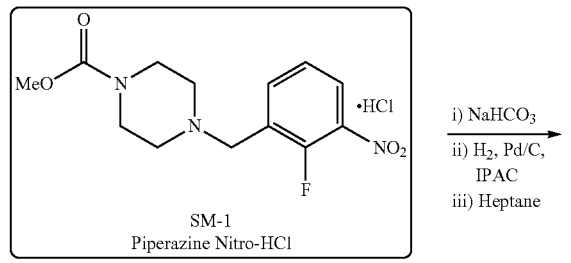

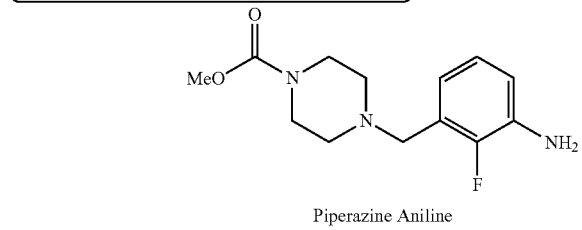

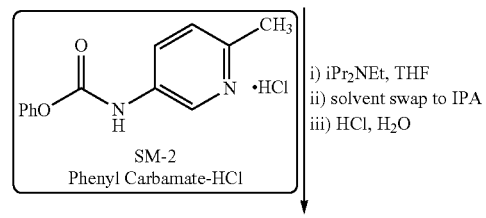

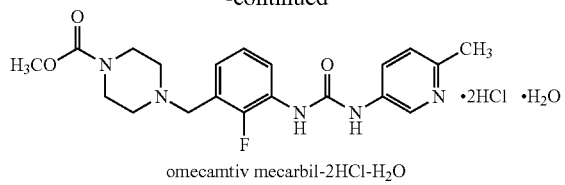

omecamtiv mecarbil-2HCl-H₂O

Synthesis of the API SM Piperazine Nitro-HCl

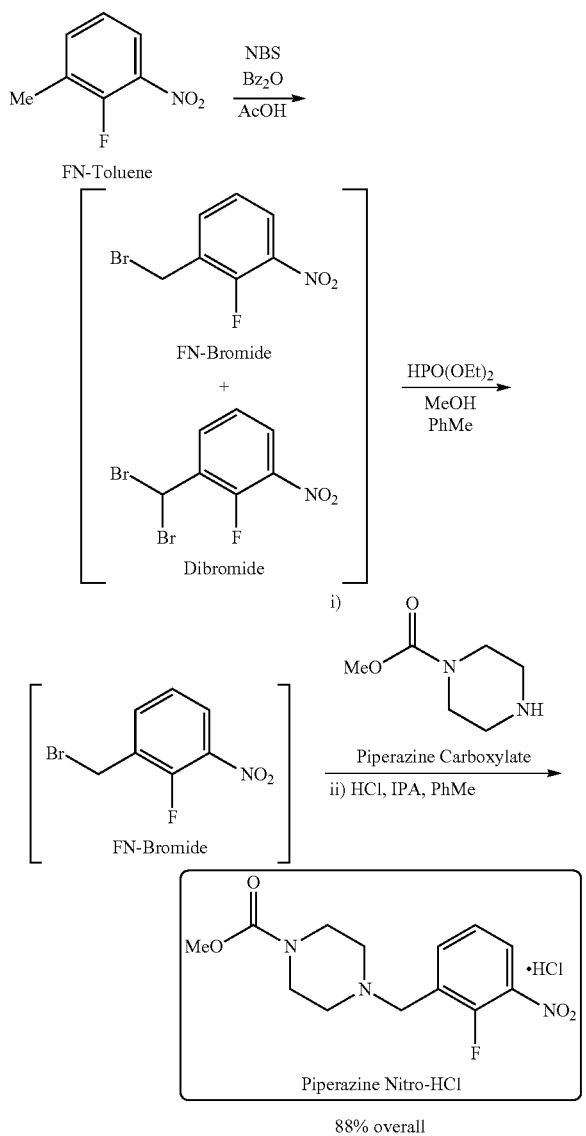

88% overall

General Methods

Reagents and solvents were used as received from commercial sources. ¹H NMR spectra were recorded on a 400 MHz spectrometer. Chemical shifts are reported in ppm from tetramethylsilane with the solvent resonance as the internal standard (CDCl₃, DMSO-d₆). Data are reported as follows: chemical shift, multiplicity (s=singlet, d=doublet, t=triplet, q=quartet, br=broad, m=multiplet), coupling constants (Hz) and integration. ¹³C NMR spectra were recorded on a 100 MHz spectrometer with complete proton decoupling. Chemical shifts are reported in ppm from tetramethylsilane with the solvent as the internal reference (CDCl₃, DMSO-d₆). All solvent charges are made with respect to starting 2-Fluoro-3-nitrotoluene.

X-Ray powder diffraction data (XRPD) were obtained using a PANalytical X'Pert PRO diffractometer (PANalytical, Almelo, The Netherlands) fitted with a real time multiple strip (RTMS) detector. The radiation used was CuKα (1.54 Å) and the voltage and current were set at 45 kV and 40 mA, respectively. Data were collected at room temperature from 5 to 45 degrees 2-theta with a step size of 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of 0.0334 degrees. Samples were prepared on a low background sample holder and placed on the sample stage which was rotated with a 2 second revolution time.

Alternatively, XRPD data were obtained using a PANalytical X'Pert PRO diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 5 to 40, degrees 2-theta with a step size of 0.0167 degrees. Samples were prepared on a low background sample holder and placed on the sample stage which was rotated with a 2 second revolution time.

Alternatively, XRPD data were obtained using a PANalytical X'Pert Pro diffractometer (PANalytical, Almelo, The Netherlands) fitted with a RTMS detector. The radiation used was CuKα (1.54 Å) and the voltage and current were set at 45 kV and 40 mA, respectively. Data were collected at room temperature from 3 to 40, degrees 2-theta with a step size of 0.008 degrees. Samples were prepared on a low background sample holder and placed on the sample stage with a 2 second revolution time.

Alternatively, XRPD data were obtained using a Bruker D8 Discover X-ray diffraction system (Bruker, Billerica, Mass.) fitted with a motorized xyz sample stage and a GADDS area detector. The radiation used was CuKα (1.54 Å) and the voltage and current were set at 45 kV and 40 mA, respectively. The solid samples on a flat glass plate were mapped and for each sample an area of 1 mm² was scanned in an oscillating mode for 3 minutes from 5 to 48 degrees 2-theta.

Differential Scanning calorimetry (DSC) data was collected using standard DSC mode (DSC Q200, TA Instruments, New Castle, Del.). A heating rate of 10° C./min was employed over a temperature range from 40° C. to 300° C. Analysis was run under nitrogen and samples were loaded in standard, hermetically-sealed aluminum pans. Indium was used as a calibration standard.

Alternatively, DSC data were collected using temperature-modulated DSC mode (DSC Q200, TA Instruments, New Castle, Del.). After sample equilibration at 20° C. for five minutes, the heating rate of 3° C./min was employed with a modulation of +/−0.75° C./min over a temperature range from 20° C. to 200° C. Analysis was run under nitrogen and samples were loaded in standard, uncrimped aluminum pans. Indium was used as a calibration standard.

FN-Bromide

In a 60 L reactor (containing no exposed Stainless steel, Hastelloy®, or other metal parts) equipped with a reflux/return condenser and scrubber charged with a 5N NaOH solution, a mechanically stirred mixture of FN-Toluene (2.0 kg, 12.89 mol, 1.0 equiv.), N-Bromosuccinimide (3.9 kg, 21.92 mol, 1.70 equiv.), benzoyl peroxide (125.0 g, 0.03 equiv., 0.39 mol, containing 25 wt % water), and acetic acid (7.0 L, 3.5 volumes) was heated to 85° C. under an atmosphere of nitrogen for 7 hours. A solution of $H_3PO_3$ (106.0 g, 1.29 mol, 0.1 equiv.) and acetic acid (200 mL, 0.1 volume), prepared in separate vessel, was added. The reaction mixture was agitated for 0.5 h and analysis of an aliquot confirmed complete decomposition of benzoyl peroxide (not detected, $HPLC_{254\ nm}$). The reaction mixture was cooled to 22° C. DI Water (8.0 L, 4 volumes) and toluene (16.0 L, 8 volumes) were charged, the biphasic mixture was agitated (20 min), and the layers were separated. Aqueous 1.6N NaOH (14.0 L, 7.0 volumes) was added to the organic layer at a rate allowing the batch temperature to stay under 25° C. and the pH of the resultant aqueous phase was measured 11). The biphasic mixture was filtered through a 5 µm Teflon® cartridge line and the layers were separated. The filter line was washed with another 2 L of toluene.

The assay yields were 2.5% of FN-Toluene, 62.3% of FN-Bromide and 30.0% of Di-Bromide. The toluene solution contained no benzoyl peroxide, succinimide, or cc bromoacetic acid and water content by KF titration was 1030 ppm (This solution could be held under nitrogen at room temperature for >12 h without any change in the assay yield).

To this solution at room temperature was added diisopropylethylamine (880.0 g, 6.63 mol, 0.53 equiv.) followed by methanol (460 mL, 11.28 mol, 0.88 equiv.) and heated to 40° C. A solution of diethylphosphite (820.0 g, 5.63 mol, 0.46 equiv.) in methanol (460 mL, 11.28 mol, 0.88 equiv.) was prepared and added to the reaction mixture at 40° C. through an addition funnel over a period of 1 hour at such a rate that the batch temperature was within 40±5° C. The contents were stirred for a period of 3 h at 40° C. from the start of addition and cooled to room temperature and held under nitrogen atmosphere for 12 hours. The assay yield of the reaction mixture was 2.5% FN-Toluene 92.0% FN-Bromide and 0.2% Di-Bromide. This solution is used as such for the alkylation step.

Characterization for Components of Final Product Mixture (Collected for Pure Compounds).

2-Fluoro-3-Nitrotoluene (FN-Toluene): $^1H$ NMR (400 MHz, CHLOROFORM-d) δ ppm 2.37 (s, 1H), 7.13-7.20 (m, 1H), 7.45-7.51 (m, 1H), 7.79-7.85 (m, 1H). $^{13}C$ NMR (100 MHz, CHLOROFORM-d) δ ppm 14.3 (d, J=5 Hz), 123.3 (d, J=3 Hz), 123.6 (d, J=5 Hz), 128.2 (d, J=16 Hz), 136.7 (d, J=5 Hz), 137.5 (broad), 153.7 (d, J=261 Hz); 1-(bromomethyl)-2-fluoro-3-nitrobenzene (FN-Bromide): $^1H$ NMR (400 MHz, CHLOROFORM-d) δ ppm 4.56 (s, 1H), 7.28-7.34 (m, 1H), 7.69-7.76 (m, 1H), 7.98-8.05 (m, 1H). $^{13}C$ NMR (100 MHz, CHLOROFORM-d) δ ppm 23.6 (d, J=5 Hz), 124.5 (d, J=5 Hz), 126.1 (d, J=3 Hz), 128.5 (d, J=14 Hz), 136.5 (d, J=4 Hz), 137.7 (broad), 153.3 (d, J=265 Hz). DSC: single melt at 53.59° C. Exact Mass $[C_7H_5BrFNO_2+H]^+$: calc.=233.9566, measured=233.9561; 1-(dibromomethyl)-2-fluoro-3-nitrobenzene (Dibromide): $^1H$ NMR (400 MHz, CHLOROFORM-d) δ ppm 6.97 (s, 1H), 7.39-7.45 (m, 1H), 8.03-8.10 (m, 1H), 8.16-8.21 (m, 1H). $^{13}C$ NMR (100 MHz, CHLOROFORM-d) δ ppm 29.2 (d, J=7 Hz), 124.9 (d, J=5 Hz), 127.1 (d, J=2 Hz), 132.1 (d, J=11 Hz), 135.7 (d, J=2 Hz), 137.2 (broad), 149.8 (d, J=266 Hz). DSC: single melt at 49.03° C. Exact Mass $[C_7H_4Br_2FNO_2+H]^+$: calc.=311.8671, measured=311.8666.

Piperazine Nitro-HCl:

To a mechanically stirred toluene solution (9 volumes) of FN-Bromide (prepared from previous step) in a 60 L reactor at 22° C. under an atmosphere of nitrogen, diisopropylethylamine was charged (1.90 kg, 14.69 mol, 1.14 equiv.). To this mixture a solution of piperazine carboxylate methylester (Piperazine Carboxylate) (2.03 kg, 14.05 mol, 1.09 equiv.) in toluene (1.0 L, 0.5 volumes) was added at a rate allowing the batch temperature to stay under 30.0° C. (Exothermic. During the addition, jacket temperature was adjusted to 5° C. in order to maintain batch temperature below 30° C. The mixture was agitated at 22° C. for 3 hours and analysis of an aliquot confirmed completion of the alkylation reaction (<1.0 LCAP FN-Bromide, $HPLC_{254\ nm}$). The reaction mixture was treated with aqueous $NH_4Cl$ (20 wt %, 10.0 L, 5 volumes; prepared from 2.0 kg of $NH_4Cl$ and 10.0 L of DI water), the biphasic mixture was agitated (30 min), and the layers were separated. The organic layer was sequentially washed with aqueous $NaHCO_3$ (9 wt %, 10.0 L, 5 volumes; prepared from 0.90 kg of $NaHCO_3$ and 10.0 L of DI water). The organic layer was filtered through a 5 µm Teflon® cartridge line and transferred in a drum, washed the filter line with another 1.0 L toluene and the combined toluene solution (10.0 volumes) weighed, and assayed (HPLC) to quantify Piperazine Nitro free base. The assay yield for the Piperazine Nitro-freebase is 89.0%, FN-Toluene 2.5% and FN-Bromide 0.2% with FN-Bromide undetected. The total loss of product to the aqueous washes is <1.0%. This solution under nitrogen atmosphere is stable for more than 12 h.

To a mechanically stirred toluene solution of Piperazine Nitro free base, prepared as described above, at 22° C. in a 60 L reactor under an atmosphere of nitrogen, IPA (19.4 L, 9.7 volumes) and DI water (1.0 L, 0.5 volume) were charged. The mixture was heated to 55° C. and 20% of the 1.4 equiv. of conc. HCl (Titrated prior to use and charge based on titer value; 276.0 mL, 3.21 mol) was charged. The contents were agitated for 15 min and Piperazine Nitro-HCl seed (130.0 g, 0.39 mol, 0.03 equiv.) was charged as slurry in IPA (400 mL, 0.2 volume). The mixture was agitated for 30 min and the remaining conc. HCl (80% of the charge, 1.10 L, 12.82 mol) was added over a period of 4 hours. The mixture was stirred at 55° C. for 1 h, cooled to 20° C. in a linear manner over 1.5 hours, and agitated at this temperature for 12 hours. The supernatant concentration of Piperazine Nitro-HCl was measured (2.8 mg/g). The mixture was filtered through an aurora filter equipped with a 5 µm Teflon® cloth. The mother liquor were transferred to a clean drum and assayed. The filter cake was washed twice with IPA (11.2 L, 5.6 volumes) and dried to constant weight (defined as ≤1.0% weight loss for 2 consecutive TGA measurements over a period of 2 hours) on filter with vacuum and a nitrogen sweep (14 h). The combined losses of Piperazine Nitro-HCl in the mother liquors and the washes were 2.5%. Piperazine Nitro-HCl was isolated 3.59 kg in 87.6% corrected yield with >99.5 wt % and 99.0% LCAP purity.

Methyl 4-(2-fluoro-3-nitrobenzyl)piperazine-1-carboxylate hydrochloride (Piperazine Nitro-HCl): $^1H$ NMR (300 MHz, DMSO-d) δ ppm 3.25 (br. s, 3H), 3.52-3.66 (m, 8H), 4.47 (s, 2H), 7.44-7.63 (t, 1H, J=8 Hz), 7.98-8.15 (m, 1H), 8.17-8.34 (m, 1H). $^{13}C$ NMR (75 MHz, DMSO-d) δ ppm 50.3, 51.4, 52.8, 119.6 (d, J=14 Hz), 125.1 (d, J=5 Hz), 127.9, 137.4 (d, J=8 Hz), 139.8 (d, J=3 Hz), 152.2, 154.7, 155.7. DSC: melt onset at 248.4° C. Exact Mass $[C_{13}H_{16}FN_3O_4+H]^+$: calculated=298.1203, measured=298.1198.

Piperazine Nitro Freebase:

In a 60 L reactor equipped with a reflux/return condenser, a mixture of Piperazine Nitro-HCl (2.0 kg, 5.99 mol, 1.0 equiv.) and isopropyl acetate (6.0 L, 3.0 volumes) was mechanically agitated at ambient temperature under an atmosphere of nitrogen. A solution of sodium bicarbonate (629 g, 7.49 mol, 1.25 equiv.) and water (7.5 L, 3.75 volume), prepared in separate vessel, was added. The biphasic mixture was agitated (15 min), and the layers were separated. The upper organic layer (containing product) was transferred to a separate vessel while the reactor was rinsed with water and isopropanol. The organic layer was then transferred through an inline 5 µm Teflon® cartridge back into the clean 60 L reactor. The filter line was washed with 4.0 L (2.0 volumes) of isopropanol into the 60 L reactor. An additional 12.0 L (6.0 volumes) of isoproponal was added to the 60 L reactor and heated to 40° C. Under reduced pressure (50 torr) the batch was concentrated down to approximately 6 L (3.0 volumes). The solution was cooled from 27° C. to 20° C. in a linear manner over 10 minutes. Water (4.0 L, 2.0 volumes) was added at 20° C. over 30 minutes followed by Piperazine Nitro Freebase seed (18 g, 0.06 mol, 0.01 equiv). The mixture was aged for 5 minutes and the remaining water (24.0 L, 12.0 volumes) was added over 90 minutes. After holding overnight at 20° C., the supernatant concentration of Piperazine Nitro Freebase was measured (<10 mg/mL). The mixture was filtered through an aurora filter equipped with a 12 μm Teflon® cloth. The filter cake was washed with a mixture of water (3.3 L, 1.65 volumes) and isopropanol (700 mL, 0.35 volumes) and dried to constant weight (defined as ≤1.0% weight loss for 2 consecutive TGA measurements over a period of 2 hours) on filter with vacuum and a nitrogen sweep (48 h). The combined losses of Piperazine Nitro Freebase in the mother liquors and the wash were approximately 7.5%. Piperazine Nitro Freebase was isolated 1.67 kg in 92.5% corrected yield with 100.0 wt % and 99.4% LCAP purity.

Synthesis of the API SM Phenyl Carbamate-HCl

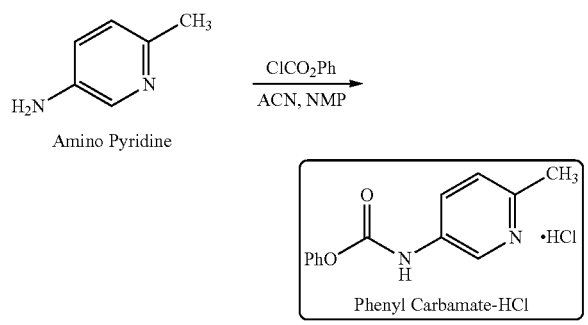

A 60 L, glass-lined, jacketed reactor set at 20° C. under nitrogen atmosphere and vented through a scrubber (containing 5N NaOH) was charged with 2.5 kg of Amino Pyridine (1.0 equiv, 23.1 moles), followed by 25 L (19.6 kg, 10 vol) acetonitrile. After initiating agitation and (the endothermic) dissolution of the Amino Pyridine, the vessel was charged with 12.5 L of N-methyl-2-pyrolidinone (12.8 kg, 5 vol). An addition funnel was charged with 1.8 L (0.6 equiv, 13.9 moles) phenyl chloroformate which was then added over 68 minutes to the solution of the Amino Pyridine keeping the internal temperature ≤30° C. The reaction was agitated for >30 minutes at an internal temperature of 20±5° C. The vessel was then charged with 61±1 g of seed as a slurry in 200 mL acetonitrile and aged for ≥30 min. The addition funnel was charged with 1.25 L (0.45 equiv, 9.7 moles) of phenyl chloroformate which was then added over 53 minutes to the reaction suspension while again keeping the temperature ≤30° C. The contents of the reactor were aged ≥30 hours at 20±5° C. After assaying the supernatant (≤15 mg/g for both product and starting material), the solids were filtered using an Aurora filter equipped with a 12 μm Teflon cloth. The mother liquor was forwarded to a $2^{nd}$ 60 L, glass-lined, jacketed reactor. The reactor and cake were rinsed with 1×10 L of 5:10 NMP/ACN and 1×10 L ACN. The washes were forwarded to the $2^{nd}$ reactor as well. The cake was dried under vacuum with a nitrogen bleed for ≥24 hours to afford 5.65 kg (90.2% yield) of the product, Phenyl Carbamate-HCl as an off-white solid in 98.8 wt % with 99.2% LCAP purity.

Phenyl (6-methylpyridin-3-yl)carbamate hydrochloride (Phenyl Carbamate-HCl) $^1$H NMR (400 MHz, DMSO-$d_6$) δ ppm 11.24 (s, 1H), 8.81 (s, 1H), 8.41 (d, 1H, J=8.8 Hz), 7.85 (d, 1H, J=8.8 Hz), 7.48-7.44 (m, 2H), 7.32-7.26 (m, 3H), 2.69 (s, 3H); $^{13}$C NMR (100 MHz, DMSO-$d_6$) δ ppm 151.66, 150.01, 147.51, 136.14, 133.79, 129.99, 129.49, 127.75, 125.87, 121.70, 18.55: HR-MS: Calculated for $C_{13}H_{12}N_2O_2$: 228.0899, M+H$^+$=229.0972; Observed mass: 229.0961

GMP Steps

Methyl 4-(3-amino-2-fluorobenzyl)piperazine-1-carboxylate (Piperazine Aniline)

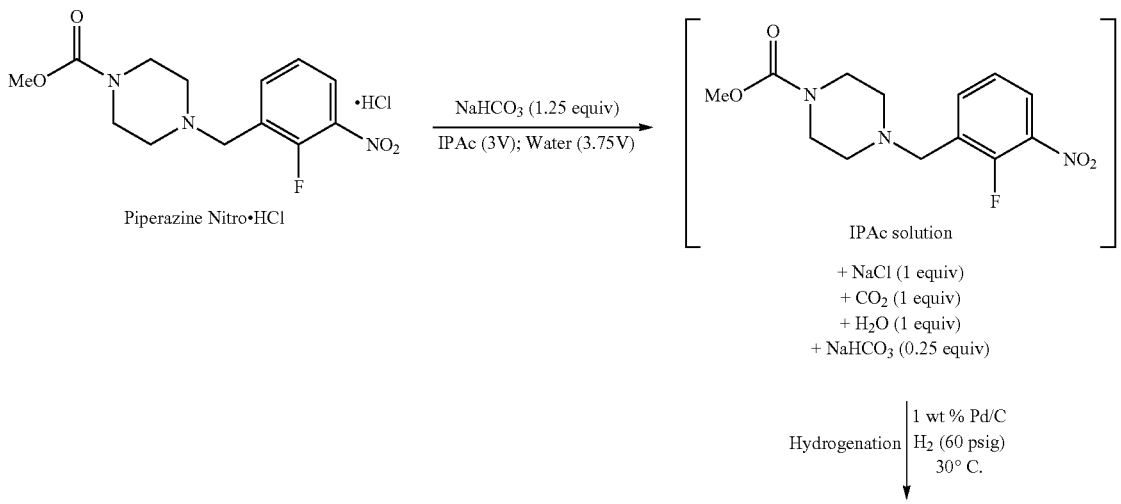

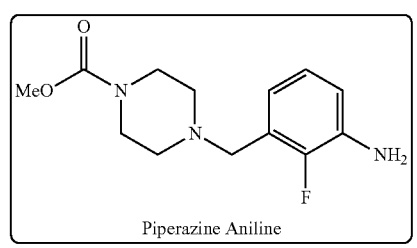 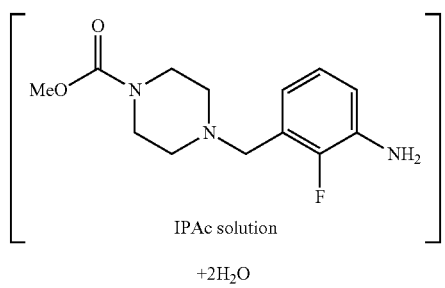

Piperazine Aniline — IPAc solution +2H₂O

Isolation
1) Azeotropic Drying (IPAc)
2) Heptane (anti-solvent)

To a 100-L jacketed glass-lined reactor were added methyl 4-(2-fluoro-3-nitrobenzyl)piperazine-1-carboxylate hydrochloride (2.00 kg, 1.00 equiv) and isopropyl acetate (6.00 L, 3.00 Vol with-respect to starting material). The resulting slurry was agitated under a nitrogen sweep. To the mixture was added dropwise over 45±30 min: 7.7% w/w aqueous sodium bicarbonate solution (629 g, 1.25 equiv of sodium bicarbonate dissolved in 7.50 L water), maintaining an internal temperature of 20±5° C. by jacket control (NOTE: addition is endothermic, and may evolve up to 1 equiv of carbon dioxide gas). The mixture was stirred for ≥15 min, resulting in a clear biphasic mixture. Agitation was stopped and the layers were allowed to settle.

The bottom (aqueous) layer was drained and analyzed by pH paper to ensure that the layer is pH>6. Quantititative HPLC analysis of the upper (organic) layer revealed 97-100% assay yield of the methyl 4-(2-fluoro-3-nitrobenzyl)piperazine-1-carboxylate freebase (1.73-1.78 kg). The upper (organic) layer was transferred through an in-line filter into a 20-L Hastelloy® hydrogenator, and the 100-L reactor and lines were rinsed with an additional aliquot of isopropyl acetate (2.00 L, 1.00 Vol). The hydrogenator was purged with nitrogen and vented to atmospheric pressure. To the reaction mixture was added a slurry of 5.0 wt % palladium on carbon (20.0 g, Strem/BASF Escat™ 1421, approx 50% water) in isopropyl acetate (400 mL), followed by a 400 mL rinse. The resulting reaction mixture was diluted with an additional aliquot of isopropyl acetate (1.2 L; total isopropyl acetate amount is 10.0 L, 5.00 Vol). The hydrogenator was purged three times with nitrogen (pressurized to 60±10 psig, then vented to atmospheric pressure), then pressurized to 60±5 psig with hydrogen. The reaction mixture was stirred at <100 rpm at 30±5° C. while maintaining 60±5 psig hydrogen, for >2 hours until reaction was deemed complete. This temperature and pressure correspond to a measured kLa value of approx 0.40 in a 20-L Hydrogenator. End of reaction is determined by dramatic decrease in hydrogen consumption accompanied by a relief in the heat evolution of the reaction. To control potential dimeric impurities, the reaction is continued for at least 30 minutes after this change in reaction profile, and HPLC analysis is performed to confirm that >99.5% conversion of the hydroxyl-amine to the aniline is achieved.

At the end of reaction, the hydrogenator was purged with nitrogen twice (pressurized to 60±10 psig, then vented to atmospheric pressure). The crude reaction mixture was filtered through a 5 μm filter followed by a 0.45 μm filter in series, into a 40-L glass-lined reactor. The hydrogenator and lines were washed with an additional aliquot of isopropyl acetate (2.00 L). Quantitative HPLC analysis of the crude reaction mixture revealed 95-100% assay yield (1.52-1.60 kg aniline product). The reaction mixture was distilled under reduced pressure (typically 250-300 mbar) at a batch temperature of 50±5° C. until the total reaction volume was approximately 8.00 L (4.00 Vol). The batch was subjected to a constant-volume distillation at 50±5° C., 250-300 mbar, by adding heptane to control the total batch volume. After approximately 8.00 L (4.00 Vol) of heptane were added, GC analysis indicated that the solvent composition was approximately 50% isopropyl acetate, 50% heptane. Vacuum was broken, and the internal batch temperature was maintained at 50±5° C. To the reaction mixture was added a slurry of seed (20.0 grams of product methyl 4-(3-amino-2-fluorobenzyl)piperazine-1-carboxylate, in a solvent mixture of 80 mL heptane and 20 mL isopropyl acetate). The resulting slurry was allowed to stir at 50±5° C. for 2±1 hours, then cooled to 20±5° C. over 2.5±1.0 h. Additional heptane (24.0 L, 12.0 Vol) was added dropwise over 2 hours, and the batch was allowed to stir at 20±5° C. for ≥1 hours (typically overnight). Quantitative HPLC analysis of this filtered supernatant revealed <5 mg/mL product in solution, and the product crystals were 50-400 μm birefringent rods. The reaction slurry was filtered at 20° C. onto a filter cloth, and the cake was displacement-washed with heptane (6.00 L, 2.00 Vol). The cake was dried on the filter under nitrogen sweep at ambient temperature for >4 hours, until sample dryness was confirmed by LOD analysis (indicated <1.0 wt % loss). The product methyl 4-(3-amino-2-fluorobenzyl)piperazine-1-carboxylate (1.56 kg) was isolated as a paleyellow powder in 86% yield at 99.8 wt % by HPLC with 100.0 LCAP$_{210}$. [Analysis of the combined filtrates and washes revealed 108 grams (7.0%) of product lost to the mother liquors. The remaining mass balance is comprised of product hold-up in the reactor (fouling).] $^1$H NMR (DMSO-d$_6$, 400 MHz) δ: 6.81 (dd, J=7.53, 7.82 Hz, 1H), 6.67 (m, 1H), 6.49 (m, 1H), 5.04 (s, 2H), 3.58 (s, 3H), 3.45 (m, 2H), 3.34 (m, 4H), 2.33 (m, 4H). $^{19}$F NMR (d$_6$-DMSO, 376 MHz) δ: −140.2. $^{13}$C NMR (d$_6$-DMSO, 125 MHz) δ: 155.0, 150.5, 148.2, 136.2 (m), 123.7 (m), 117.6, 115.1, 73.7, 54.9 (m), 52.1 (m), 43.4. mp=89.2° C.

Omecamtiv Mecarbil Dihydrochloride Hydrate Procedure

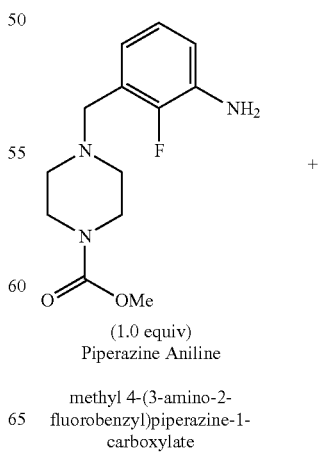

(1.0 equiv)
Piperazine Aniline methyl 4-(3-amino-2-fluorobenzyl)piperazine-1-carboxylate

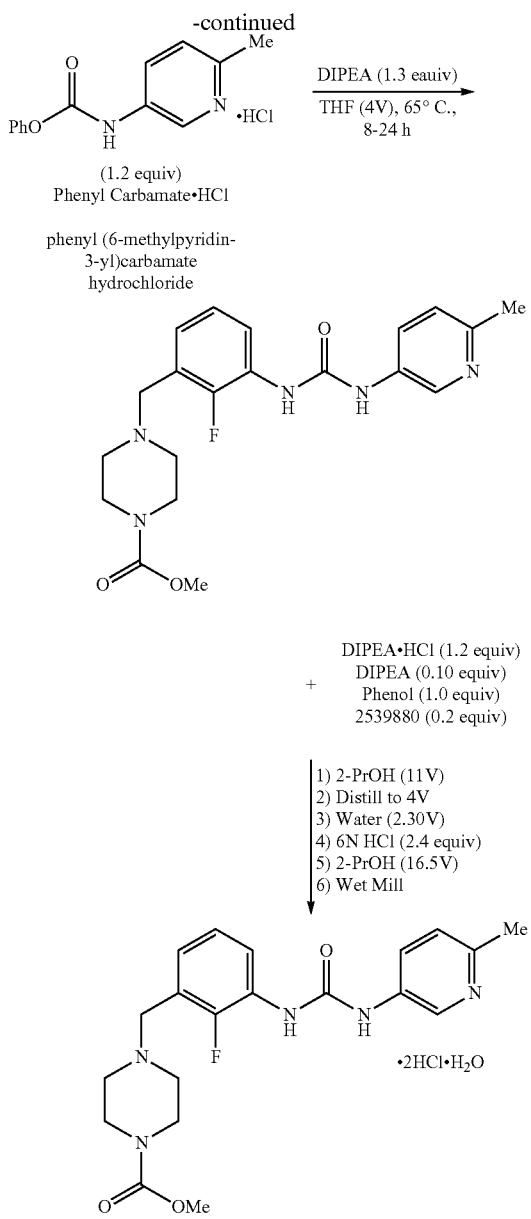

To a 15 L glass lined reactor were charged methyl 4-(3-amino-2-fluoro-benzyl)piperazine-1-carboxylate (1,202 g, 4.50 mol), phenyl (6-methylpyridin-3-yl)carbamate hydrochloride (1,444 g, 5.40 mol), and tetrahydrofuran (4.81 L). The resulting slurry was agitated under a nitrogen sweep and N,N-diisopropylethylamine (1,019 L, 5.85 mol) was then charged to the slurry which resulted in a brown solution. The temperature of the solution was increased to 65° C. and agitated for 22 h, until <1% AUC piperazine aniline remained by HPLC analysis.

The batch was cooled to 50° C. and distilled under reduced pressure while maintaining the internal temperature of the vessel below 50° C. by adjusting vacuum pressure. 2-Propanol was added with residual vacuum at a rate to maintain a constant volume in the 15 L reactor. A total of 10.5 kg of 2-propanol was required to achieve <5% THF by GC. Water (2.77 kg) was then charged to the reactor followed by the addition of 6N HCl (1.98 kg) at a rate to maintain the internal temperature below 60° C. The reactor was brought to ambient pressure under a nitrogen sweep. The solution was then heated to 60° C., and transferred to a 60 L glass lined reactor through an inline filter. The 15 L reactor was then rinsed with 1:1 water/2-propanol (1.2 L) which was sent through the inline filter to the 60 L reactor.

The 60 L reactor was adjusted to 45° C. and a slurry of seed (114 g, 0.23 mol) in 2-propanol (0.35 L) was added to the reactor resulting in a slurry. The batch was aged at 45° C. for 1 h, followed by the addition of 2-propanol (3.97 kg) through an inline filter over 2 h. The batch was heated to 55° C. over 1 h and held for 0.25 h, then cooled back to 45° C. over 1 h and held overnight at 45° C. 2-propanol (11.71 kg) was then added through an inline filter to the batch over 3 h. The batch was aged for 1 h and then cooled to 20° C. over 2 h and held at 20° C. for 0.5 h. The batch was then recirculated though a wet mill affixed with 1-medium and 2-fine rotor-stators operating at 56 Hz for 2.15 h, until no further particle size reduction was observed by microscopy.

The batch was then filtered through a 20" Hastelloy® filter fitted with a 12 um filter cloth under 500 torr vacuum. A wash solution of 95:5 2-propanol:water (1.82 L) was charged through an inline filter to the 60 L reactor, then onto the filter. A second wash of 2-propanol (2.85 L) was charged through an inline filter to the 60 L reactor, then onto the filter. The batch was then dried under 5 psi humidified nitrogen pressure until <5,000 ppm 2-propanol, and 2.5-5% water remained. The final solid was discharged from the filter to afford 2.09 kg of methyl 4-(2-fluoro-3-(3-(6-methylpyridin-3-yl)ureido)benzyl)piperazine-1-carboxylate as an off-white crystalline solid in 89% yield at 99.88 wt % by HPLC, 100.0% AUC. Total losses to liquors was 0.10 kg (4.7%).

DSC: $T_{onset}$=61.7° C., $T_{max}$=95.0° C.; TGA=2.2%, degradation onset=222° C.; $^1$H HMR (D$_2$O, 500 MHz) δ 8.87 (s, 1H), 8.18 (d, J=8.9 Hz, 1H), 7.83 (t, J=7.5 Hz, 1H), 7.71 (d, J=8.8 Hz, 1H), 7.35-7.29 (m, 2H), 4.48 (s, 2H), 4.24 (br s, 2H), 3.73 (s, 3H), 3.31 (br s, 6H), 2.68 (s, 3H); $^{13}$C HMR (D$_2$O, 150 MHz) δ 156.8, 154.2, 153.9 (J=249 Hz), 147.8, 136.3, 136.1, 130.1, 129.4, 128.0, 127.2, 125.5 (J=11.8 Hz), 125.1 (J=4.2 Hz), 116.1 (J=13.5 Hz), 53.54, 53.52, 53.49, 50.9, 40.5, 18.2.

Comparative Example 1: Immediate Release Formulation

TABLE 1

| Material | Theo. w/w % | Theo. mg/unit |
| --- | --- | --- |
| Intra-granulation | | |
| omecamtiv mecarbil dihydrochloride hydrate | 12.28 | 30.70 |
| Fumaric acid | 12.28 | 30.70 |
| Microcrystalline cellulose, Avicel ® PH 101 | 38.00 | 95.00 |
| Lactose monohydrate, Impalpable 313 | 29.94 | 74.85 |
| Hydroxypropyl cellulose, Klucel EXF | 2.00 | 5.00 |
| Croscarmellose sodium, Ac-Di-Sol | 2.50 | 6.25 |
| Extra-granulation | | |
| Croscarmellose sodium, Ac-Di-Sol | 2.50 | 6.25 |
| Magnesium stearate | 0.50 | 1.25 |
| Total | 100.00% | 250.00 |

Immediate release formulation comprising the above components were prepared according to the process outlined in FIG. 1.

Example 1: Prototype Modified Release Formulation

Omecamtiv mecarbil prototype modified release ("MR") matrix tablet formulation consists of omecamtiv mecarbil anhydrate free base (active), Methocel™ K100 M CR (control release agent), citric acid monohydrate (pH modulation agent), microcrystalline cellulose and lactose monohydrate (filler), Methocel™ E5 LV (binder), and magnesium stearate (lubricant). Table 1 shows the prototype formulation compositions. The prototype MR matrix tablets are manufactured via a conventional high shear wet granulation process. This includes screening omecamtiv mecarbil anhydrate, lactose monohydrate FFL 316, microcrystalline cellulose, Avicel® PH 101, Methocel™ K100 M CR, and citric acid monohydrate through a #20 mesh US standard screen followed by charging the screened materials into an appropriate size of high shear granulator, where the materials are dry mixed for a specific time at the pre-determined impeller and chopper speeds (granulator size, dry mixing time, impeller and chopper speeds are scale-dependent parameters). The wet granulation process starts with the addition of pre-prepared 3% w/w Methocel™ E5 solution using a pre-selected spray nozzle at a pre-determined spray pressure and spray rate. The pre-determined impeller and chopper speeds are used during the wet granulation process (the nozzle size, spray rate, spray pressure, impeller, and chopper speeds are scale-dependent parameters). After wet granulation, the wet mass is dried using a fluid bed drying process with a target of LOD (loss on drying) of <2.4% (fluid bed granulator is scale-dependent The dried granulation is then milled using a Fitzmill® using a pre-determined speed and screen size (Fitzmill® model, speed and screen size are scale-dependent parameters). After milling, the milled dry granulation is lubricated using the pre-screened (#30 mesh) magnesium stearate in a tumble blender at a pre-determined speed, time, and fill-volume (tumble blender model, blending speed, time, and fill-volume are scale-dependent parameters). After the lubrication, the final blend is compressed into MR matrix tablets using a rotary tablet press at a target tablet hardness of 10-14 kp.

The following case study exemplifies an embodiment of a manufacturing process of omecamtiv mecarbil anhydrate 25 mg prototype MR matrix tablets. The target batch size is 60 kg. the raw materials billed for the batch is 4.30 kg of omecamtiv mecarbil anhydrate (approximately 14.7% excess to compensate the de-lumping loss), 10.1 kg of microcrystalline cellulose, Avicel® PH101, 8.12 kg of lactose monohydrate FFL316, 7.50 kg of citric acid monohydrate, 30.0 kg of Methocel™ K100 M CR, 0.6 kg Methocel™ E5 LV (excess binder solution prepared, but the exact amount is added during wet granulation process. The residual binder solution is discarded as the waste), 19.4 kg of purified water, and 0.30 kg of magnesium stearate.

Binder solution preparation: Filling 19.4 kg of purified water into a 19-gallon portable mixing kettle and then adding 0.6 kg of Methocel™ E5 LV slowly and steadily.

Loading the raw materials into the Diosna P-300 high shear granulator: Manually loading the majority of screened lactose monohydrate and microcrystalline cellulose into granulator bowl. Manually loading citric acid monohydrate into the bowl. Manually loading milled omecamtiv mecarbil anhydrate into the bowl. Manually loading screened Methocel™ K100 M CR into the bowl.

Transferring the binder solution: Transferring the binder solution into the solution tank.

Wet granulation: Transferring 6.60 kg of binder solution into granulator bowl.

Fluid bed drying: Dry the granulation.

Dry milling: Manually charging the dried granulation and beginning to mill.

Lubrication: Loading approximately half of the milled granulation into a V-blender and then adding the magnesium stearate in, adding the remaining half of milled granulation in.

Compression: The final blend is manually charged into the hopper of rotary tablet press equipped with 7/16" round, standard cup, concave, plain tooling. The target tablet weight is 400 mg with a range of 370-430 mg. the target hardness is 12 kp with a range of 10-14 kp.

Prototype MR Matrix Tablet Formulation Composition

| Component | 12.5 mg % w/w | 25.0 mg % w/w |
|---|---|---|
| omecamtiv mecarbil anhydrate | 3.125 | 6.25 |
| MCC, Avicel ® PH101 | 16.88 | 16.88 |
| Lactose monohydrate FFL 316 | 18.25 | 13.55 |
| Citric acid Monohydrate | 6.25 | 12.50 |
| Methocel ™ K100 M CR | 50.00 | 50.00 |
| Methocel ™ E5 LV | 5.00 | 0.33 |
| Magnesium stearate | 0.50 | 0.50 |

Matrix Modified Release Tablet: General Method

A process for modified release ("MR") matrix tablet manufacturing via a dry granulation process is described herein. Omecamtiv mecarbil dihydrochloride hydrate, microcrystalline cellulose, lactose monohydrate, Methocel™ K100 M CR/Methocel™ K100 LV CR, and fumaric acid are screened and then charged into a tumble blender and blended there for a specific time at a pre-determined speed (blender size, blending speed, and blending time are scale-dependent parameters). The blended materials are lubricated in the same blender using the pre-screened magnesium stearate. The lubricated blend is then roller compacted and milled. The resultant granulation is lubricated in a tumble blender using the pre-screened magnesium stearate. The lubricated granulation is compressed into modified release matrix tablets using a rotary tablet press with a target tablet hardness of 10 kp.

Example 2: Omecamtiv Mecarbil Dihydrochloride Hydrate 25 Mg Slow Release MR Matrix Tablets (MTX-F1)

The target batch size is 5 kg the raw materials billed for the batch is 306.50 g of omecamtiv mecarbil dihydrochloride hydrate, 1840.50 g of microcrystalline cellulose, Avicel® PH102, 920.0 g of lactose monohydrate, FFL316, 383.0 g of fumaric acid, 1500.0 g of Methocel™ K100 M CR, 35 g of intra-granular magnesium stearate (10 g excess from theoretical batch size to accommodate the screening process loss), and 35 g of extra-granular magnesium stearate (10 g excess from theoretical batch size to accommodate the screening process loss).

Powder Screening: Step 1. Screening 1840.5 g of microcrystalline cellulose, Avicel® PH102, 306.50 g of omecamtiv mecarbil dihydrochloride hydrate, 383.11 g of fumaric acid, 920.0 g of lactose monohydrate, FFL316, and 1500.0 g of Methocel™ K100 M CR through a 20 mesh US standard sieve into a double PE bag.

Powder Blending: Step 2. Charging the screened blend from Step 1 into a 20 L Bohle blender and blending for 30 minutes at a speed of 20 rpm.

Powder Lubrication: Step 3. Screening the entire amount of intra-granular magnesium stearate through a 60 mesh US standard sieve and weighing out the required amount of sieved magnesium stearate, 25.0 g, into a an appropriate container. Step 4. Manually pre-mixing the required amount of sieved magnesium stearate with approximately 1× to 3× of powder blend from Step 2 in the same container for approximately 60 seconds. Step 5. Charging the pre-mix blend from Step 4 back into the powder blend in Step 2. Step 6. Blending the powder blend from Step 2 for 4 minutes at a blending speed of 20 rpm. Step 7. Discharging the lubricated powder blend into an appropriate container.

Dry granulation: Step 8. Charging the lubricated powder blend from Step 7 into Gerteis roller compactor hopper and start dry granulation manufacturing using the following process parameters. Roll Surface: Knurl; Agitator speed: 15 rpm; Roll force: 7.0 kn/cm; Roll speed: 2 rpm; Roll gap: 2.5 mm; Gap control: ON; Screen size: 1 mm; Clearance between granulator and screen: 2.0 mm; Granulator speed: 80 rpm; and Granulator rotation angle: 200/230 degree. Step 9. Discharging the granulation into an appropriate container and weigh the net weight, which is 4844 g.

Granulation lubrication: Step 10. Calculating the required amount of magnesium stearate needed for the granulation blend, which is 24.34 g. Step 11. Screening the entire amount of extra-granular magnesium stearate through a 60 mesh US standard sieve and weighing out the required amount of screened magnesium stearate in Step 10. Step 12. Charging the granulation from Step 9 into a 20 liter Bohle blender. Step 13. Manually pre-mixing the screened extra-granular magnesium stearate from Step 11 with 1× to 3× of granulation from Step 12 in an appropriate container for about 60 seconds. Step 14. Charging the pre-mixed blend from Step 13 back to the blender in Step 12. Step 15. Blending the granulation blend from Step 12 for 5 minutes at a blending speed of 20 rpm. Step 16. Discharging the granulation blend from Step 15 into an appropriate container.

Tablet compression: Step 17. The final granulation blend from Step 16 is manually charged into the hopper of rotary tablet press Korsch XL100 equipped with 7/16" round, standard cup, concave, plain tooling. Step 18. The compression starts at a speed of 25 rpm to dial in the target tablet weight and hardness. The target tablet weight is 500 mg with a range of 475-525 mg. the target hardness is 10 kp with a range of 6-14 kp. The total number of tablet manufactured is 9,115.

TABLE 2

Composition of omecamtiv mecarbil dihydrochloride hydrate 25 mg slow release MR matrix tablets MTX-F1 in accordance with the disclosure

| Material | 25 mg Slow release | |
|---|---|---|
| | Theo. w/w (%) | Theo. mg/unit |
| Intra-granular | | |
| omecamtiv mecarbil Di-HCl hydrate | 6.13 | 30.65 |
| Methocel ™ K100 M Prem CR | 30.00 | 150.00 |
| Microcrystalline cellulose, PH 102 | 36.81 | 184.05 |
| Lactose monohydrate, FF 316 | 18.40 | 92.00 |
| Fumaric acid | 7.66 | 38.30 |
| Magnesium stearate | 0.50 | 2.50 |
| Sub Total | 99.50 | 497.50 |
| Extra-granular | | |
| Magnesium stearate | 0.50 | 2.50 |
| Total/batch weight | 100.00 | 500.00 |

Figure 2:
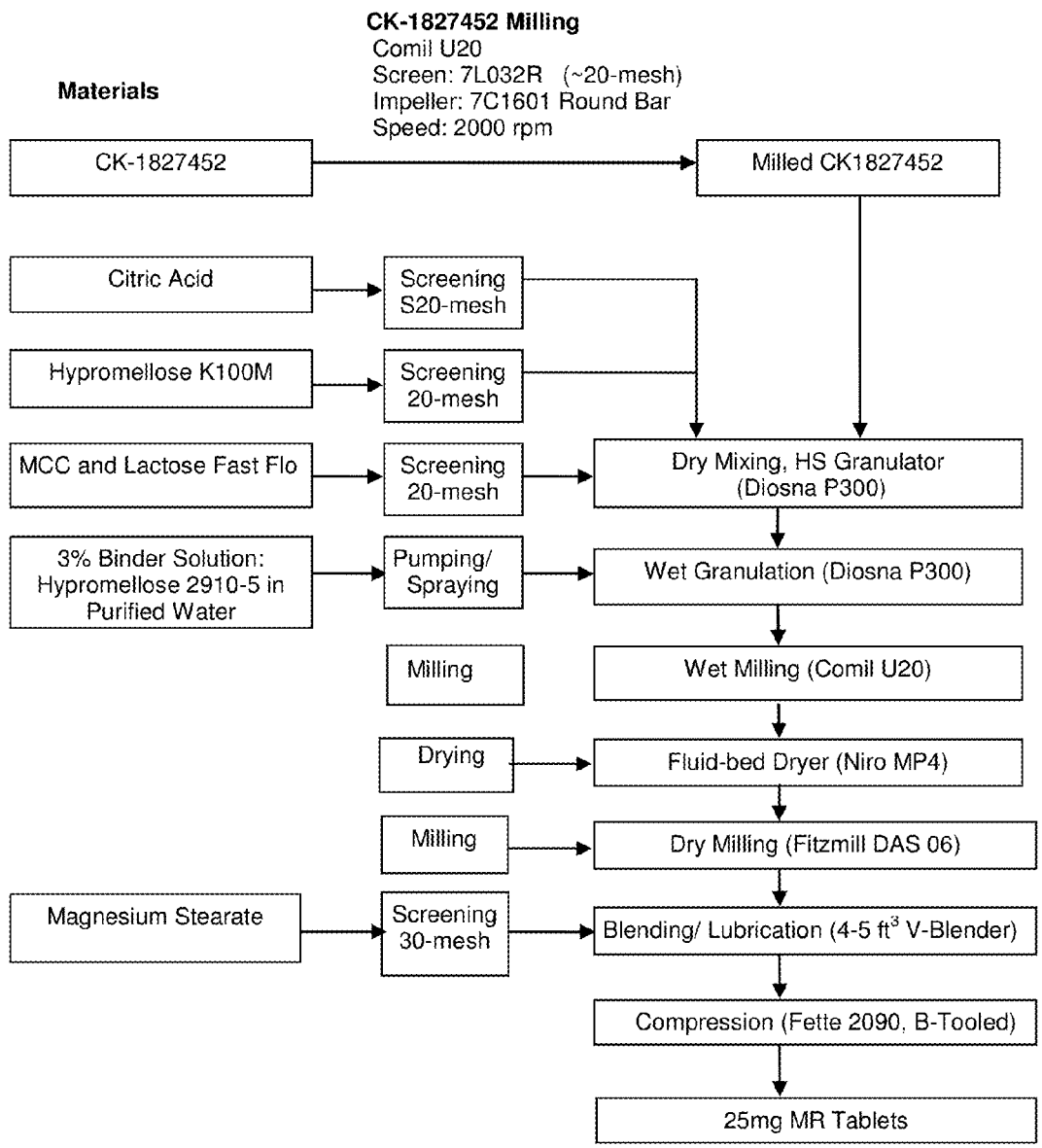
FIG. 2 is a flow diagram for the preparation of matrix modified release compositions; see Example 2.

Matrix modified release tablets comprising the above components were prepared according to the process outlined in FIG. 2. Note: In some embodiments, the concentration range is 15%-80% for Methocel™ K100 M CR, 0%-70% for microcrystalline cellulose, Avicel® PH102, 0%-70% for lactose monohydrate, FFL316, 3.83%-50% for fumaric acid, 0%-2% for intra-granular magnesium stearate, and 0%-2% for extra-granular magnesium stearate.

Example 3

TABLE 3

Composition of omecamtiv mecarbil dihydrochloride hydrate 25 mg fast release MR matrix tablets MTX-F2 in accordance with the disclosure

| Material | 25 mg Fast release | |
|---|---|---|
| | Theo. w/w (%) | Theo. mg/unit |
| Intra-granular | | |
| omecamtiv mecarbil Di-HCl hydrate | 6.13 | 30.65 |
| Methocel ™ K100 M Prem CR | 5.00 | 25.00 |
| Methocel ™ K100 LV Prem CR | 20.00 | 100.00 |
| Microcrystalline cellulose, PH 102 | 40.14 | 200.70 |
| Lactose monohydrate, FF 316 | 20.07 | 100.35 |
| Fumaric acid | 7.66 | 38.30 |
| Magnesium stearate | 0.50 | 2.50 |
| Sub Total | 99.50 | 497.50 |
| Extra-granular | | |
| Magnesium stearate | 0.50 | 2.50 |
| Total/batch weight | 100.00 | 500.00 |

Figure 3:
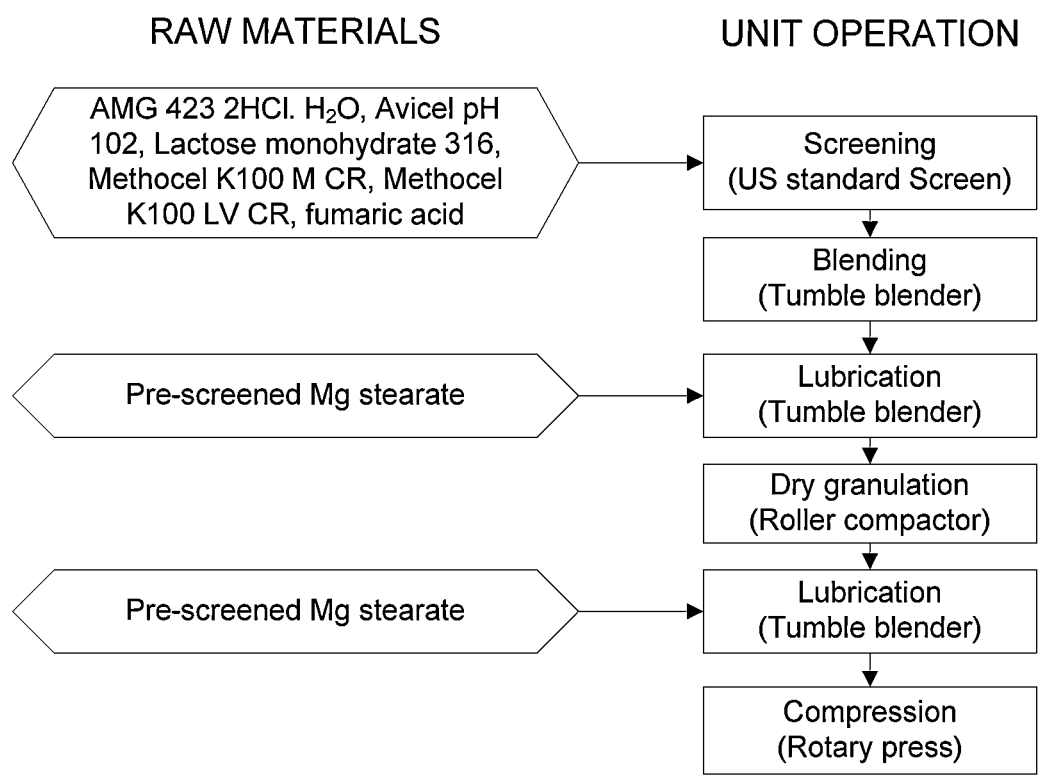
FIG. 3 is a flow diagram for the preparation of matrix modified release compositions; see, Examples 3-5.
Figure 4:
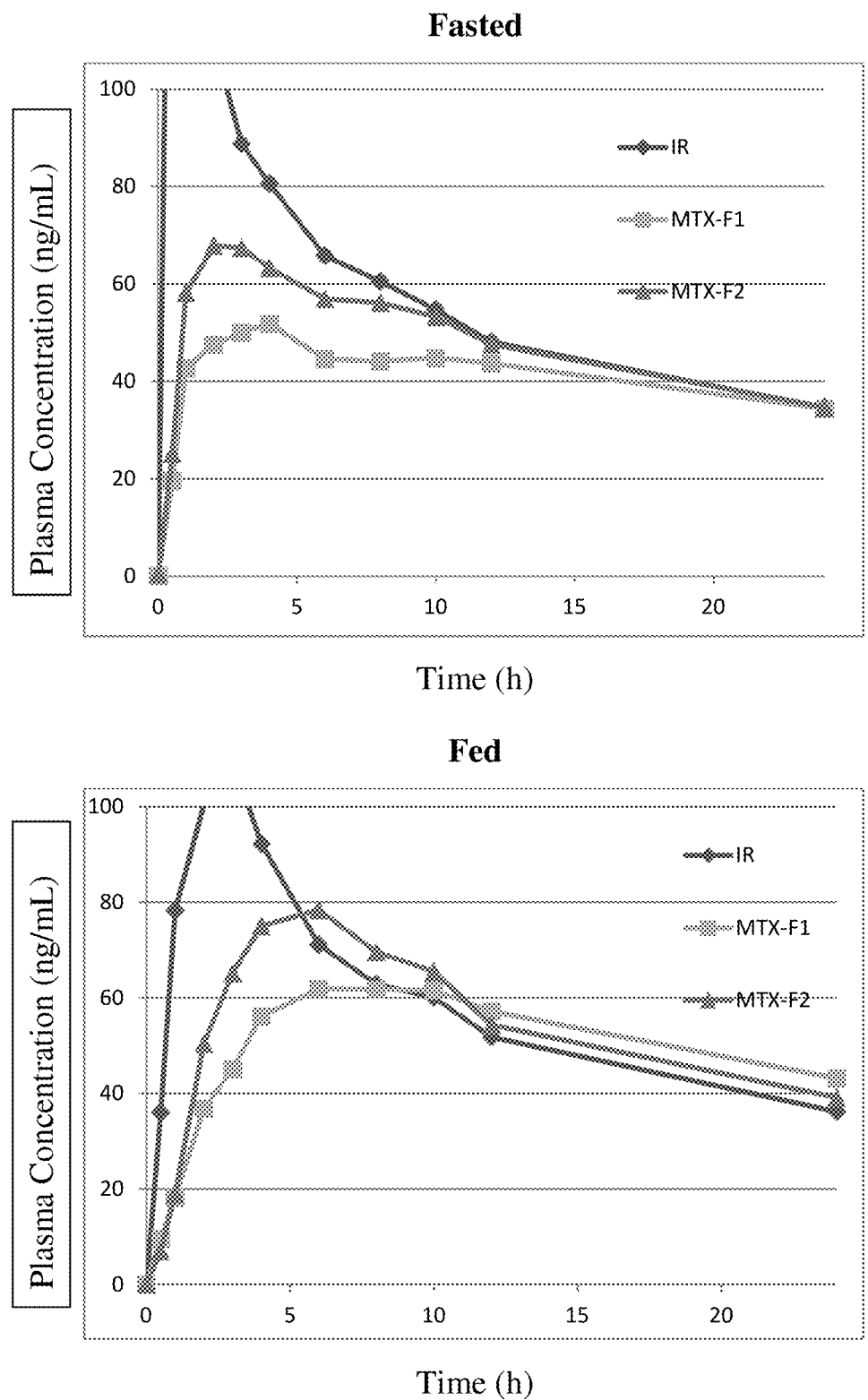
FIG. 4 shows the exposure of healthy volunteers (plasma concentration (ng/ml) v. time (h)), fasted (top) and fed (bottom) for an immediate release composition (IR) and two matrix modified release compositions (MTX-F1 and MTX-F2).

Matrix modified release tablets comprising the above components were prepared according to the process outlined in FIG. 3. Note: In some embodiments, the concentration range is 0%-15% for Methocel™ K100 M CR, 15%-50% for Methocel™ K100 LV, 0%-75% for microcrystalline cellulose, Avicel® PH102, 0%-75% for lactose monohydrate, FFL316, 3.83%-50% for fumaric acid, 0%-2% for intra-granular magnesium stearate, and 0%-2% for extra-granular magnesium stearate.

Example 4

TABLE 4

Composition of omecamtiv mecarbil dihydrochloride hydrate 75 mg slow release MR matrix tablets MTX-F3 in accordance with the disclosure

| Material | 75 mg | |
|---|---|---|
| | Theo. w/w (%) | Theo. mg/unit |
| Intra-granular | | |
| omecamtiv mecarbil Di-HCl hydrate | 18.37 | 91.85 |
| Methocel ™ K100 M Prem CR | 30.00 | 150.00 |
| Microcrystalline cellulose, PH 102 | 24.20 | 121.00 |
| Lactose monohydrate, FF 316 | 8.07 | 40.35 |
| Fumaric acid | 18.37 | 91.85 |
| Magnesium stearate | 0.50 | 2.50 |
| Sub Total | 99.50 | 497.50 |
| Extra-granular | | |
| Magnesium stearate | 0.50 | 2.50 |
| Total/batch weight | 100.00 | 500.00 |

Matrix modified release tablets comprising the above components were prepared according to the process outlined in FIG. 3. Note: In some embodiments, the concentration range is 15%-80% for Methocel™ K100 M CR, 0%-65% for microcrystalline cellulose, Avicel® PH102, 0%-65% for lactose monohydrate, FFL316, 3.83%-50% for fumaric acid, 0%-2% for intra-granular magnesium stearate, and 0%-2% for extra-granular magnesium stearate.

Example 5

TABLE 5

Composition of omecamtiv mecarbil dihydrochloride hydrate 75 mg fast release MR matrix tablets MTX-F4 in accordance with the disclosure

| Material | 75 mg Fast release | |
|---|---|---|
| | Theo. w/w (%) | Theo. mg/unit |
| Intra-granular | | |
| omecamtiv mecarbil Di-HCl hydrate | 18.37 | 91.85 |
| Methocel ™ K100 M Prem CR | 5.00 | 25.00 |
| Methocel ™ K100 LV Prem CR | 20.00 | 100.00 |
| Microcrystalline cellulose, PH 102 | 27.95 | 200.70 |
| Lactose monohydrate, FF 316 | 9.31 | 100.35 |
| Fumaric acid | 18.37 | 91.85 |
| Magnesium stearate | 0.50 | 2.50 |
| Sub Total | 99.50 | 497.50 |
| Extra-granular | | |
| Magnesium stearate | 0.50 | 2.50 |
| Total/batch weight | 100.00 | 500.00 |

Matrix modified release tablets comprising the above components were prepared according to the process outlined in FIG. 3. Note: In some embodiments, the concentration range is 0%-15% for Methocel™ K100 M CR, 15%-50% for Methocel™ K100 LV, 0%-65% for microcrystalline cellulose, Avicel® PH102, 0%-65% for lactose monohydrate, FFL316, 3.83%-50% for fumaric acid, 0%-2% for intra-granular magnesium stearate, and 0%-2% for extra-granular magnesium stearate.

pH Dependent Release Profiles

A formulation of omecamtiv mecarbil hemihydrate (free base) and dihydrochloride hydrate (Form A) were prepared having the following components, all components reported as a w/w %:

Free Base (75 mg matrix tablet) Active granulation: 15.37% free base; 30% hypromellose, HPMC K100 MPrem CR; 10% citric acid monohydrate; 11.88% microcrystalline cellulose, Avicel PH 101; 6.75% lactose monohydrate, FastFlo 316; 12.5% purified water; and Citric Acid granulation: 20% citric acid monohydrate; 5% microcrystalline cellulose, Avicel PH 101; and 1% magnesium stearate, non-bovine.

Form A (75 mg matrix tablet) Intra-granulation: 18.37% Form A; 30% hypromellose, HPMC K100 MPrem CR; 0.50% magnesium stearate; and Extra-granulation: 16.88% microcrystalline cellulose, Avicel PH 101; 18.37% citric acid anhydrous; and 0.5% magnesium stearate, non-bovine.

Figure 6:
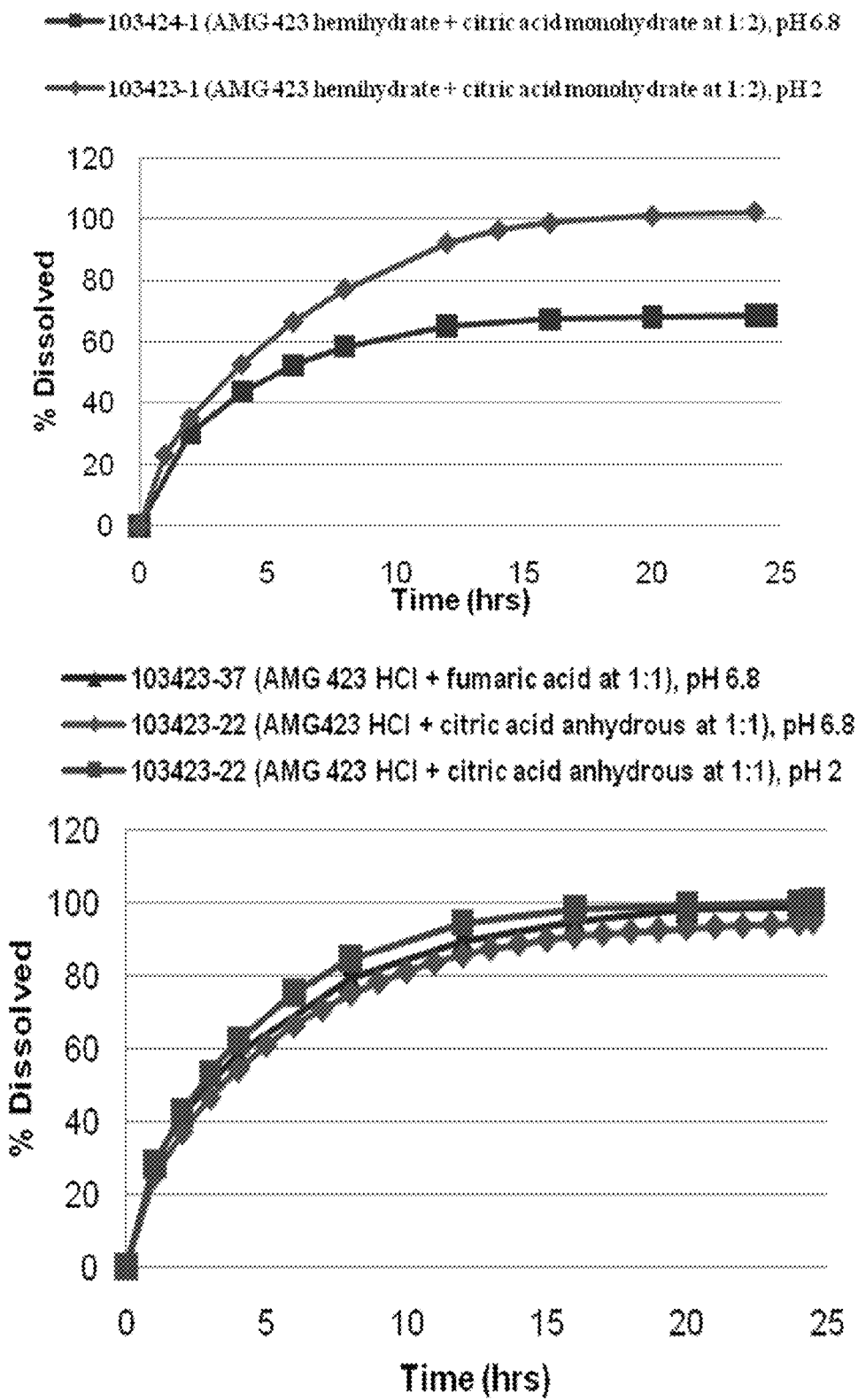
FIG. 6 shows drug release at two pHs (2 and 6.8) for a matrix formulation of omecamtiv mecarbil free base (top) and for a omecamtiv mecarbil dihydrochloride hydrate salt form, Form A (bottom).

The formulations were tested at pH 2 and pH 6.8 and the amount of drug released over time was measured. The results of this drug release profile are shown in FIG. 6.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed:
1. An oral pharmaceutical formulation comprising:
   omecamtiv mecarbil dihydrochloride hydrate;
   a control release agent;
   a pH modifying agent comprising maleic acid, fumaric acid, tartaric acid, glutamic acid, or a combination thereof;
   a filler; and
   a lubricant.
2. A pharmaceutical formulation according to claim 1, wherein the pH modifying agent is fumaric acid.
3. A pharmaceutical formulation according to claim 1, wherein the filler is selected from starches, lactose, mannitol, cellulose derivatives, calcium phosphate, a sugar, and any combination thereof.
4. A pharmaceutical formulation according to claim 1, wherein the control release agent comprises hypromellose having a viscosity of 100,000 mPa·s at 2% concentration in water at 20° C.
5. A pharmaceutical formulation according to claim 1, wherein the control release agent comprises hypromellose having a viscosity of 100 mPa·s at 2% concentration in water at 20° C.
6. A pharmaceutical formulation according to claim 1, wherein the control release agent is a mixture of hypromellose having a viscosity of 100,000 mPa·s at 2% concentration in water at 20° C. and hypromellose having a viscosity of 100 mPa·s at 2% concentration in water at 20° C.
7. A pharmaceutical formulation according to claim 1, wherein the filler is a combination of microcrystalline cellulose and lactose monohydrate.
8. A pharmaceutical formulation according to claim 1, wherein the lubricant is magnesium stearate.
9. The pharmaceutical formulation according to claim 1, in the form of a tablet.
10. The pharmaceutical formulation according to claim 1 comprising:
   3-30% w/w omecamtiv mercarbil dihydrochloride hydrate;
   15-35% w/w control release agent;
   20-45% w/w pH modifying agent;
   25-65% w/w filler; and
   0.1-1.0% w/w lubricant.
11. The pharmaceutical formulation according to claim 1, having a weight ratio (w/w %:w/w %) of the pH-modifying agent to the omecamtiv mecarbil dihydrochloride hydrate, of less than 2:1 to 1:1.
12. The pharmaceutical formulation according to claim 11, having a weight ratio of the pH-modifying agent to the omecamtiv mecarbil dihydrochloride hydrate, of 1:1.
13. The pharmaceutical formulation according to claim 1, comprising:
   5-7% w/w omecamtiv mecarbil dihydrochloride hydrate;
   27-33% w/w control release agent;
   52-58% w/w filler;
   6-9% w/w fumaric acid; and
   0.2-2% w/w lubricant.
14. The pharmaceutical formulation according to claim 13, wherein the control release agent comprises hypromellose having a viscosity of 100,000 mPa·s at 2% concentration in water at 20° C.
15. The pharmaceutical formulation according to claim 13, wherein the control release agent comprises hypromellose having a viscosity of 100 mPa·s at 2% concentration in water at 20° C.
16. The pharmaceutical formulation according to claim 13, wherein the filler comprises microcrystalline cellulose.
17. The pharmaceutical formulation according to claim 13, wherein the filler comprises lactose monohydrate.
18. The pharmaceutical formulation according to claim 1, comprising:

17-20% w/w omecamtiv mecarbil dihydrochloride hydrate;
21-29% w/w control release agent;
34-41% w/w filler;
17-20% w/w fumaric acid; and
0.2-2% w/w lubricant.

19. The pharmaceutical formulation according to claim 18, wherein the control release agent comprises hypromellose having a viscosity of 100,000 mPa·s at 2% concentration in water at 20° C.

20. The pharmaceutical formulation according to claim 18, wherein the control release agent comprises hypromellose having a viscosity of 100 mPa·s at 2% concentration in water at 20° C.

21. The pharmaceutical formulation according to claim 18, wherein the filler comprises microcrystalline cellulose.

22. The pharmaceutical formulation according to claim 18, wherein the filler comprises lactose monohydrate.

23. The pharmaceutical formulation according to claim 1, comprising:
12-25% w/w omecamtiv mecarbil dihydrochloride hydrate;
25-35% w/w control release agent;
25-40% w/w filler;
12-25% w/w fumaric acid; and
0.2-4% w/w lubricant.

24. The pharmaceutical formulation according to claim 1, comprising:
3-10% w/w omecamtiv mecarbil dihydrochloride hydrate;
20-40% w/w control release agent;
42-67% w/w filler;
4-11% w/w fumaric acid; and
0.2-4% w/w lubricant.

25. The pharmaceutical formulation according to claim 1, comprising:
12-25% w/w omecamtiv mecarbil dihydrochloride hydrate;
13-37% w/w control release agent;
24-50% w/w filler;
12-25% w/w fumaric acid; and
0.2-4% w/w lubricant.

26. An oral pharmaceutical formulation comprising:
omecamtiv mecarbil dihydrochloride hydrate;
a control release agent;
a pH modifying agent comprising maleic acid, fumaric acid, tartaric acid, glutamic acid, or a combination thereof;
a filler; and
a lubricant, wherein
the control release agent comprises (a) hypromellose having a viscosity of 100,000 mPa.s at 2% concentration in water at 20° C., (b) hypromellose having a viscosity of 100 mPa.s at 2% concentration in water at 20° C., or (c) a mixture of (a) and (b); and
the filler comprises (a) microcrystalline cellulose, (b) lactose monohydrate, or (c) a mixture of (a) and (b).

27. The pharmaceutical formulation according to claim 26, comprising:
3-30% w/w omecamtiv mercarbil dihydrochloride hydrate;
15-35% w/w control release agent;
20-45% w/w pH modifying agent;
25-65% w/w filler; and
0.1-1.0% w/w lubricant.

28. The pharmaceutical formulation according to claim 26, comprising:
5-7% w/w omecamtiv mecarbil dihydrochloride hydrate;
27-33% w/w control release agent;
52-58% w/w filler;
6-9% w/w fumaric acid; and
0.2-2% w/w lubricant.

29. The pharmaceutical formulation according to claim 26, comprising:
17-20% w/w omecamtiv mecarbil dihydrochloride hydrate;
21-29% w/w control release agent;
34-41% w/w filler;
17-20% w/w fumaric acid; and
0.2-2% w/w lubricant.

30. The pharmaceutical formulation according to claim 26, comprising:
12-25% w/w omecamtiv mecarbil dihydrochloride hydrate;
25-35% w/w control release agent;
25-40% w/w filler;
12-25% w/w fumaric acid; and
0.2-4% w/w lubricant.

31. The pharmaceutical formulation according to claim 26, comprising:
3-10% w/w omecamtiv mecarbil dihydrochloride hydrate;
20-40% w/w control release agent;
42-67% w/w filler;
4-11% w/w fumaric acid; and
0.2-4% w/w lubricant.

32. The pharmaceutical formulation according to claim 26, comprising:
12-25% w/w omecamtiv mecarbil dihydrochloride hydrate;
13-37% w/w control release agent;
24-50% w/w filler;
12-25% w/w fumaric acid; and
0.2-4% w/w lubricant.

33. The pharmaceutical formulation according to claim 1, in the form of a tablet, and wherein the pH modifying agent is fumaric acid, the control release agent is a mixture of hypromellose having a viscosity of 100,000 mPa.s at 2% concentration in water at 20° C. and hypromellose having a viscosity of 100 mPa.s at 2% concentration in water at 20° C.; the filler is a combination of microcrystalline cellulose and lactose monohydrate; and the lubricant is magnesium stearate.

* * * * *